(12) United States Patent
Akin et al.

(10) Patent No.: US 10,434,641 B2
(45) Date of Patent: Oct. 8, 2019

(54) IN SITU GAP INSPECTION ROBOT SYSTEM AND METHOD

(71) Applicant: General Electric Company, Schenectady, NY (US)

(72) Inventors: Selim Akin, Istanbul (TR); Thomas James Batzinger, Burnt Hills, NY (US); Airton Rosa da Silva, Jr., Schenectady, NY (US); Selami Haydar Icli, Zurich (CH); Christopher Paul Markman, Canton, GA (US); Paulo Cesar Debenest, Tokyo (JP); Michele Guarnieri, Tokyo (JP); Shigeo Hirose, Tokyo (JP)

(73) Assignee: General Electric Company, Schenectady, NY (US)

(*) Notice: Subject to any disclaimer, the term of this patent is extended or adjusted under 35 U.S.C. 154(b) by 154 days.

(21) Appl. No.: 15/652,680

(22) Filed: Jul. 18, 2017

(65) Prior Publication Data
US 2019/0022849 A1   Jan. 24, 2019

(51) Int. Cl.
*B25J 5/00* (2006.01)
*G01R 31/34* (2006.01)

(52) U.S. Cl.
CPC ............. *B25J 5/005* (2013.01); *G01R 31/34* (2013.01)

(58) Field of Classification Search
CPC ............ B25J 5/00; G01R 31/34; F01D 25/00
USPC ................................. 280/124.125
See application file for complete search history.

(56) References Cited

U.S. PATENT DOCUMENTS

| 4,677,865 | A | | 7/1987 | Lehmann | |
|---|---|---|---|---|---|
| 4,683,973 | A | * | 8/1987 | Honjo | B62D 7/026 180/252 |
| 4,889,000 | A | * | 12/1989 | Jaafar | G01R 31/34 73/865.8 |
| 4,970,890 | A | | 11/1990 | Jaafar et al. | |
| 5,172,639 | A | | 12/1992 | Wiesman et al. | |
| 5,650,579 | A | * | 7/1997 | Hatley | B62D 55/065 348/E7.086 |
| 5,788,002 | A | | 8/1998 | Richter | |

(Continued)

FOREIGN PATENT DOCUMENTS

| CH | 669127 A5 | 2/1989 |
|---|---|---|
| EP | 0171633 A1 | 2/1986 |

(Continued)

OTHER PUBLICATIONS

International Search Report and written opinion for corresponding PCT Application No. PCT/US2018/037900 dated Sep. 13, 2018, 14 pages.

(Continued)

*Primary Examiner* — Stephen Holwerda
(74) *Attorney, Agent, or Firm* — Juergen Hoffmann; Hoffman Warnick LLC

(57) ABSTRACT

Systems and methods for in situ gap inspection in a machine, such as a generator, an electric motor, or a turbomachine are described. A robotic crawler has multidirectional traction modules, an expandable body, and sensor modules. A control system communicates with the robotic crawler to provide a control signal to navigate an inspection path within an annular gap of the machine. The inspection path includes axial and radial movements to inspect the annular gap using the sensor modules.

25 Claims, 14 Drawing Sheets

(56) References Cited

U.S. PATENT DOCUMENTS

| | | |
|---|---|---|
| 5,947,051 A | 9/1999 | Geiger |
| 5,969,531 A | 10/1999 | Murakami et al. |
| 6,100,711 A | 8/2000 | Hatley |
| 6,404,189 B2 | 6/2002 | Kwun et al. |
| 6,814,169 B2 | 11/2004 | Moore et al. |
| 6,876,222 B2 | 4/2005 | Fischer et al. |
| 6,889,783 B1 | 5/2005 | Moore et al. |
| 6,917,176 B2 | 7/2005 | Schempf et al. |
| 6,959,603 B2 | 11/2005 | Knight et al. |
| 7,188,568 B2 | 3/2007 | Stout |
| 7,201,055 B1 | 4/2007 | Bagley et al. |
| 7,218,993 B2 | 5/2007 | Yasukawa et al. |
| 7,331,436 B1 * | 2/2008 | Pack .................. B65H 75/425 191/12.2 A |
| 7,520,189 B2 | 4/2009 | Abbasi et al. |
| 7,600,593 B2 | 10/2009 | Filippov et al. |
| 7,624,827 B2 | 12/2009 | Moser et al. |
| 7,654,348 B2 | 2/2010 | Ohm et al. |
| 7,681,452 B2 | 3/2010 | Bagley et al. |
| 7,743,675 B2 | 6/2010 | Moore |
| 7,866,421 B2 | 1/2011 | Moore et al. |
| 7,891,445 B1 | 2/2011 | McKinley et al. |
| 8,028,775 B2 | 10/2011 | Orenbuch |
| 8,220,345 B2 | 7/2012 | Moser et al. |
| 8,477,891 B2 | 7/2013 | Wallace et al. |
| 8,568,299 B2 | 10/2013 | Eno et al. |
| 8,571,711 B2 | 10/2013 | Jacobsen et al. |
| 8,839,684 B2 | 9/2014 | Banowetz et al. |
| 9,031,698 B2 | 5/2015 | Smith |
| 9,056,746 B2 | 6/2015 | Mehrandezh et al. |
| 9,217,852 B2 | 12/2015 | Baleine |
| D748,053 S | 1/2016 | Herrlich et al. |
| D756,922 S | 5/2016 | Herrlich et al. |
| 9,398,198 B2 | 7/2016 | Choi et al. |
| 9,683,460 B2 | 6/2017 | Moore et al. |
| 9,708,934 B2 | 7/2017 | Moore et al. |
| 9,759,667 B2 | 9/2017 | Miasnikov et al. |
| 9,808,140 B2 | 11/2017 | Belson et al. |
| 2002/0104693 A1 | 8/2002 | Moore et al. |
| 2002/0190682 A1 | 12/2002 | Schempf et al. |
| 2004/0020002 A1 * | 2/2004 | Moore .................. B62D 57/024 15/340.1 |
| 2004/0099175 A1 | 5/2004 | Perrot et al. |
| 2004/0173116 A1 | 9/2004 | Ghorbel et al. |
| 2005/0104600 A1 | 5/2005 | Cotton |
| 2008/0087112 A1 | 4/2008 | Bagley et al. |
| 2008/0098832 A1 * | 5/2008 | Abbasi .................. H02K 15/00 73/865.9 |
| 2008/0121041 A1 | 5/2008 | Smith et al. |
| 2008/0179115 A1 | 7/2008 | Ohm et al. |
| 2008/0308324 A1 | 12/2008 | Moser et al. |
| 2009/0120215 A1 | 5/2009 | Jacobson et al. |
| 2009/0146680 A1 * | 6/2009 | Moser .................. G01R 31/34 324/765.01 |
| 2009/0171151 A1 | 7/2009 | Choset et al. |
| 2011/0040427 A1 | 2/2011 | Ben-Tzvi |
| 2013/0231779 A1 | 9/2013 | Purkayastha et al. |
| 2014/0022374 A1 | 1/2014 | Brignac et al. |
| 2014/0067185 A1 | 3/2014 | Tralshawala et al. |
| 2014/0216836 A1 | 8/2014 | Davies et al. |
| 2014/0345384 A1 | 11/2014 | Nguyen |
| 2015/0233787 A1 | 8/2015 | Eakins et al. |
| 2015/0251318 A1 | 9/2015 | Lv |
| 2015/0323469 A1 | 11/2015 | Clayton et al. |
| 2016/0075020 A1 | 3/2016 | Szarski et al. |
| 2016/0239080 A1 | 8/2016 | Marcolina et al. |
| 2017/0362068 A1 | 12/2017 | Cheng |
| 2018/0021945 A1 | 1/2018 | Pettersen et al. |

FOREIGN PATENT DOCUMENTS

| | | |
|---|---|---|
| EP | 0390352 A2 | 10/1990 |
| EP | 1863153 A2 | 12/2007 |
| EP | 2345902 A1 | 7/2011 |
| EP | 2743447 A1 | 6/2014 |
| FR | 2355236 A1 | 1/1978 |
| JP | 2007256262 A | 10/2007 |
| WO | 9702452 | 1/1997 |
| WO | 2008076193 A2 | 6/2008 |
| WO | 2015095543 A1 | 6/2015 |
| WO | 2016038529 A1 | 9/2016 |
| WO | 2016141769 A1 | 9/2016 |

OTHER PUBLICATIONS

U.S. Appl. No. 15/652,859, Office Action dated Feb. 19, 2019, 17 pages.

International Search Report and written opinion for corresponding PCT Application No. PCT/US2018/041726 dated Oct. 29, 2018, 16 pages.

International Search Report and written opinion for corresponding PCT Application No. PCT/US2018/035329 dated Sep. 11, 2018, 18 pages.

International Search Report and written opinion for corresponding PCT Application No. PCT/US2018/038453 dated Oct. 25, 2018, 17 pages.

International Search Report and written opinion for corresponding PCT Application No. PCT/US2018/040982 dated Oct. 17, 2018, 15 pages.

U.S. Appl. No. 15/652,730, Notice of Allowance dated May 3, 2019, 9 pages.

International Search Report and Written Opinion for PCT Application No. PCT/DK96/00298 dated Oct. 17, 1996, 25 pages.

U.S. Appl. No. 15/652,859, Notice of Allowance dated May 15, 2019, 10 pgs.

U.S. Appl. No. 15/652,805, Office Action dated Jun. 27, 2019, 13 pgs.

* cited by examiner

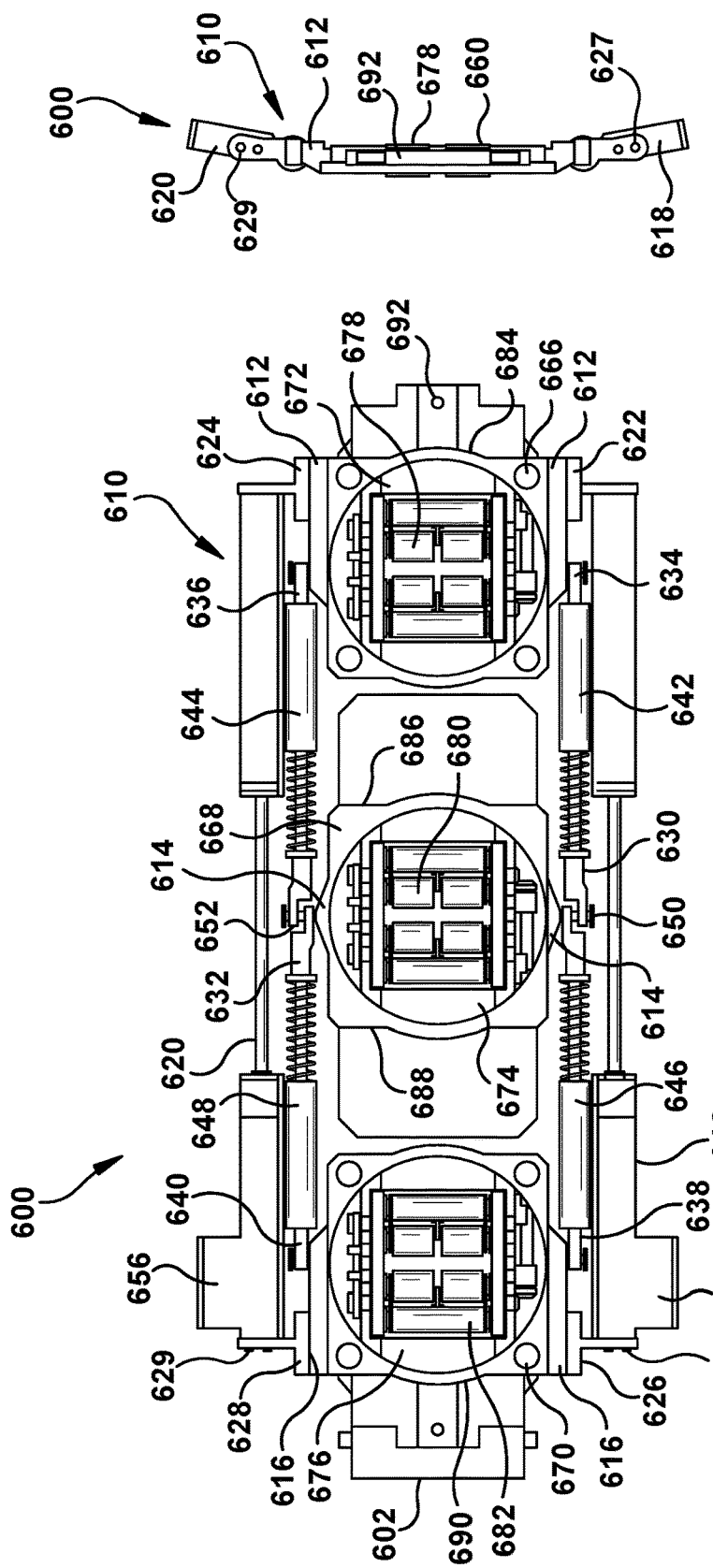

IN SITU GAP INSPECTION ROBOT SYSTEM AND METHOD

BACKGROUND OF THE INVENTION

The disclosure relates to inspection of machinery and, more specifically, inspection using a robot inserted into an annular gap space, such as an air gap, in a generator, electric motor, or turbomachine, including turbo-generators.

The disclosure is related to concurrently filed U.S. patent application Ser. No. 15/652,730, entitled "MODULAR CRAWLER ROBOT FOR IN SITU GAP INSPECTION" filed Jul. 18, 2017, the entire contents of which are incorporated herein by reference. The disclosure is related to concurrently filed U.S. patent application Ser. No. 15/652,771, entitled "END REGION INSPECTION MODULE AND METHOD FOR IN SITU GAP INSPECTION ROBOT SYSTEM" filed Jul. 18, 2017, the entire contents of which are incorporated herein by reference. The disclosure is related to concurrently filed U.S. patent application Ser. No. 15/652,859, entitled "OMNIDIRECTIONAL TRACTION MODULE FOR A ROBOT" filed Jul. 18, 2017, the entire contents of which are incorporated herein by reference. The disclosure is related to concurrently filed U.S. patent application Ser. No. 15/652,805, entitled "ACTUATED SENSOR MODULE AND METHOD FOR IN SITU GAP INSPECTION ROBOTS" filed Jul. 18, 2017, the entire contents of which are incorporated herein by reference.

A visual, mechanical, and/or electrical inspection and testing of a generator, electric motor, or turbomachine should be performed on a periodic basis. For example, generators may be inspected and tested periodically in the field for stator wedge tightness, visual surface anomalies, electromagnetic core imperfections, etc. Generator/stator inspection and testing procedures may require complete disassembly of the stator and removal of the generator rotor from the stator before any inspections or tests can be performed on the unit. The cost of disassembly and removal of the rotor, the time it takes for this process, and the dangers of rotor removal may impact the frequency of such inspections.

In situ inspection of generators has been performed employing poles, trolleys, scopes, and rotor turning techniques. These procedures may not accomplish the inspection task in a complete, timely, or safe manner.

Use of a robotic crawler capable of insertion through the radial air gap between the core iron and the retaining ring permits in situ inspection of the rotor and the stator core. The crawler may be inserted in a collapsed position into the gap and expanded by spring return pneumatic rams to the width of the air gap. The crawler may be remotely controlled by a technician and provides video cameras and other inspection tools to perform generator rotor and stator inspections within the air gap as the crawler is driven to selected locations. The crawler may be maneuvered by the technician within the air gap using video for both navigation and visual inspection.

BRIEF DESCRIPTION OF THE INVENTION

A first aspect of this disclosure provides a system for in situ gap inspection. A robotic crawler has a plurality of multidirectional traction modules, an expandable body connected to the multidirectional traction modules, and a plurality of sensor modules positioned by the plurality of multidirectional traction modules. A control system is in communication with the robotic crawler. The control system provides a control signal to the robotic crawler to navigate an inspection path within an annular gap of a machine. Navigating the inspection path includes axial movement and circumferential movement of the plurality of multidirectional traction modules to inspect the annular gap using the plurality of sensor modules.

A second aspect of the disclosure provides a method for in situ gap inspection. A robotic crawler is inserted into an annular gap of a machine. An expandable body of the robotic crawler is expanded such that a plurality of multidirectional traction modules on the robotic crawler engage opposed surfaces in the annular gap. The robotic crawler traverses an inspection path within the annular gap using axial movements and circumferential movements. A plurality of inspection tests are performed along the inspection path using a plurality of sensor modules on the robotic crawler.

A third aspect of the disclosure provides a robot control system for in situ gap inspection. A crawler configuration module provides operating instructions for a robotic crawler having a plurality of multidirectional traction modules, an expandable body connected to the multidirectional traction modules, and a plurality of sensor modules. At least one inspection path definition correlates to an inspection path within an annular gap of a machine. The machine is selected from a generator, an electric motor, or a turbomachine. An autonomous navigation module is in communication with the robotic crawler to provide a control signal for the robotic crawler to traverse the inspection path using axial movements and circumferential movements of the plurality of multidirectional traction modules to inspect the annular gap using the plurality of sensor modules.

The illustrative aspects of the present disclosure are arranged to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which:

FIG. 7 shows a top view of the robotic crawler of FIG. 6 in its collapsed state.

FIG. 8 shows an end view of the robotic crawler of FIG. 6 in its collapsed state.

Figure 1:
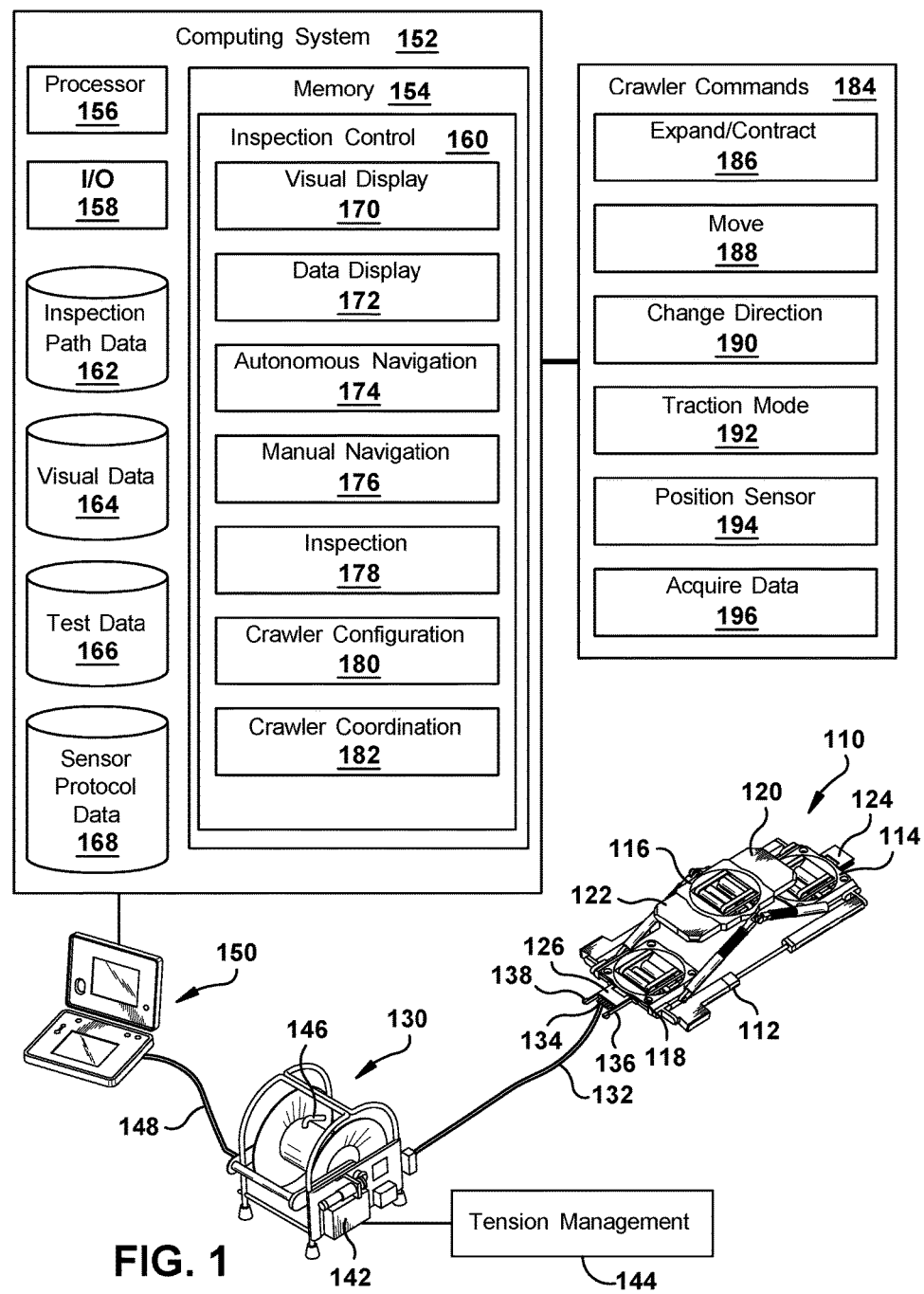
FIG. 1 shows a diagram of an example system for in situ gap inspection according to various embodiments of the disclosure.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be used and that changes may be made without departing from the scope of the present teachings. The following description is, therefore, merely illustrative.

Where an element or layer is referred to as being "on," "engaged to," "disengaged from," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Referring to FIG. 1, an example system 100 for in situ gap inspection is shown. System 100 may include a robotic crawler 110, a tether reel 130, and a control system 150. Robotic crawler 110 may be configured to be inserted through an entrance gap into an annular gap in a machine to conduct autonomous or semi-autonomous inspection of the machine. For example, robotic crawler 110 may be a collapsible robot that can operate in a collapsed or expanded state and may be inserted through a narrow entrance gap in its collapsed state and expand to a wider gap width such that it engages the opposed surfaces of the annular gap. Robotic crawler 110 is shown in its expanded state in FIG. 1. Once in the annular gap, robotic crawler 110 may navigate the annular gap and use one or more sensor modules to conduct various inspection tests during its movements or at various desired crawler positions in the annular gap. Robotic crawler 110 may be configured for multidirectional movement, including forward and reverse movement in the axial direction and bi-directional lateral movement in the circumferential direction. In some embodiments, robotic crawler 110 may be configured for omnidirectional movement that includes bi-directional movement in any orientation between the axial and circumferential directions, in addition to the axial and circumferential directions. For example, robotic crawler 110 may be configured to move in any direction in a 360 degree arc and freely change its direction of travel to any orientation in the 360 degree arc, including a plurality of directions between and angled from the axial and circumferential directions. In some embodiments, robotic crawler 110 may include a tether 132 connected to robotic crawler 110 and extending out of the machine during operation. For example, tether 132 may be a cable connected to robotic crawler 110 to enable retrieval of robotic crawler 110 in the event that robotic crawler 110 cannot navigate out of the annular gap under its own power. In some embodiments, tether 132 may provide a physical connection from robotic crawler 110 for a wired communication channel and/or a remote power source and/or pneumatic or hydraulic lines to support test systems or robotic operation. Tether reel 130 may be automated to adjust the tension and/or slack on tether 132 during operation of robotic crawler 110 within the annular gap, enabling robotic crawler 110 to navigate various navigation paths and perform inspection routines without a user manually managing the position of the tether. Control system 150 may be in communication with robotic crawler 110 to provide control signals to robotic crawler 110 and receive sensor, navigation, and/or other operational data from robotic crawler 110. In some embodiments, control system 150 may be electrically connected to tether 132 directly or through tether reel 130 and the electrical connection may include one or both of a power channel and a communication channel. Control system 150 may provide a user interface for a user to monitor, evaluate, supplement, and/or control robotic crawler 110 during an inspection deployment within the annular gap of the machine.

In some embodiments, robotic crawler 110 is a modular robot that may be reconfigured for different inspection tasks and enabling efficient maintenance, replacement, and/or upgrade of individual modules. Robotic crawler 110 may include a body frame, such as an expandable body 112, for receiving, positioning, and connecting various modules relative to one another. In some embodiments, expandable body 112 accommodates a plurality of traction modules 114, 116, 118. For example, robotic crawler 110 may include three traction modules 114, 116, 118, a forward traction module 114, a middle traction module 116, and a rear traction module 118, where forward traction module 114 and rear traction module 118 are configured to engage a first surface in the annular gap and the middle traction module 116 is configured to engage an opposed second surface in the annular gap. Traction modules 114, 116, 118 may be multidirectional traction module capable of moving robotic crawler 110 in multiple directions, including both axial and circumferential movement within the annular gap. Robotic crawler 110 may further include a plurality of sensor modules 120, 122, such as visual sensors for navigation and/or visual inspection. For example, sensor modules 120, 122 may be attached via sensor interfaces on the forward and rear sides of middle traction module 116 and may provide both forward and rear facing navigation cameras, as well as one or more upward facing cameras for inspecting the adjacent surface of the annular gap. Robotic crawler 110 may also include one or more tether connectors 124, 126 for detachably receiving tether 132, generally with a compatible end connector 134 and fasteners 136, 138.

In some embodiments, tether reel 130 is an automated tether reel that may receive, release, and spool tether 132 to adjust tension as needed during operation of robotic crawler 110. For example, tether reel 130 may include a servo motor 142 and tension management logic 144. For example, servo motor 142 operating in a torque/current control mode may detect changes in tension on tether 132 as it enters tether reel 130 and tension management logic 144 may provide an algorithm for maintaining an acceptable tension range using servo motor 142 to reel in or reel out tether 132 under closed loop control. In some embodiments, tether 132 may have a fixed connection 146 to tether reel 130 and a separate wire 148 may connect to control system 150. For example, wire 148 may provide communication and/or power channels without providing the mechanical characteristics desired for tethering robotic crawler 110. In some embodiments, tether reel 130 may provide an interface for receiving control signals for tether reel 130 from control system 150. For example, control system 150 may be able to adjust tension control or motor parameters and/or manually override operation of tether reel 130. In some embodiments, robotic crawler 110 may operate without a tether, carry its own power (e.g., batteries), and/or use wireless communication with control system 150.

In some embodiments, control system 150 may include a computing system 152. Computing system 152 may provide a plurality of programmatic controls and user interface for operating robotic crawler 110. In some embodiments, computing system 152 is a general purpose computing devices, such as a personal computer, work station, mobile device, or an embedded system in an industrial control system (using general purpose computing components and operating systems). In some embodiments, computing system 152 may be a specialized data processing system for the task of controlling operation of system 100. Computing system 152 may include at least one memory 154, processor 156, and input/output (I/O) interface 158 interconnected by a bus. Further, computing system 152 may include communication with external I/O device/resources and/or storage systems, including connected system, such as robotic crawler 110, tether reel 130, and network resources. In general, processor 156 executes computer program code, such as inspection control module 160, that is stored in memory 154 and/or a storage system. While executing computer program code, processor 156 can read and/or write data to/from memory 154, storage systems, and I/O devices (through I/O interface 158). The bus provides a communication link between each of the components within computing system 152. I/O devices may comprise any device that enables a user to interact with computing system 152 (e.g., keyboard, pointing device, display, etc.). Computing system 152 is only representative of various possible combinations of hardware and software. For example, the processor may comprise a single processing unit, or be distributed across one or more processing units in one or more locations, e.g., on a client and server. Similarly, memory and/or storage systems may reside at one or more physical locations. Memory and/or storage systems can comprise any combination of various types of non-transitory computer readable storage medium including magnetic media, optical media, random access memory (RAM), read only memory (ROM), etc. In some embodiments, computing system 152 is a laptop computer in communication with robotic crawler 110 via a wired (serial, USB, Ethernet, etc.) or wireless (802.11, Bluetooth, etc.) connection and running application software for system 100. In some embodiments, some or all of the functions of computing system 152 may be on board robotic crawler 110 using an integrated computing system, such as an on board control module, with or without wireless communication to one or more user interfaces and/or remote data storage.

In some embodiments, computing system 152 may include one or more application programs, data sources, and/or functional modules for controlling robotic crawler 110. For example, computing system 152 may include inspection control module 160 that operates in conjunction with data sources 162, 164, 166, 168 to provide control signals to and receive data from robotic crawler 110. Inspection control module 160 may provide a visual display module 170. For example, visual data collected by cameras on robotic crawler 110 may be displayed by visual display module 170, such as a graphical user interface for one or more video feeds. In some embodiments, visual data from robotic crawler 110 may be stored in visual data source 164 for use by visual display module 170 and/or selective, temporary, and/or archival storage of visual data for later use, including use by other users or systems. Data display module 172 may provide display, including visual display, of other test data, including processed visual data and resulting calculations or analysis. For example, data display module 172 may include a graphical user interface for test results from one or more test protocols using sensor and navigation data from robotic crawler 110. In some embodiments, test data from robotic crawler 110 may be stored in test data source 166 for use by data display module 172 and/or selective, temporary, and/or archival storage of test data for later use, including use by other users or systems. Data display module 172 may include a real-time display of test data as it is collected by robotic crawler 110 and/or one or more functions for viewing, aggregating, analyzing, visualizing, selecting, and/or reporting test data from test data source 166. Autonomous navigation module 174 may provide a protocol or series of commands for navigation of robotic crawler 110 within the annular gap of the machine. In some embodiments, autonomous navigation module 174 enables a user to select an inspection path from a plurality of inspection paths stored in inspection path data source 162. For example, inspection paths may be defined as physical paths robotic crawler 110 should follow within the annular gap to complete one or more inspection tasks in one or more locations within the annular gap. Inspection paths may be based on a physical schematic or parameters of one or more machines defining axial and circumferential distances. Inspection paths may also include parameters and locations related to specific features of interest for either navigation (e.g., surface features to be avoided) or for testing (e.g., locations or corresponding crawler positions for conducting specific tests). In some embodiments, inspection paths may be stored and defined in terms of a sequence of crawler commands. Autonomous navigation module 174 may enable autonomous navigation by robotic crawler 110 receiving and executing a sequence of crawler commands without user intervention once the autonomous operation is initiated. In some embodiments, autonomous navigation module 174 may have completely autonomous inspection routines that require no user intervention once initiated or may include a plurality of inspection subroutines, such as specific movement patterns, position changes, or test protocols, that are initiated in a desired sequence by a user, potentially based on navigational, visual, or test data feedback. Manual navigation module 176 may provide a user with the ability to pilot or otherwise control robotic crawler 110. In some embodiments, manual navigation module 176 may be provided for establishing an initial position for initiating automated control and/or allow a user to override automated control in response to problems, exceptions, or specific test protocols (such as an initial test result that requires further data gathering). In some embodiments, control system 150 may include one or more user I/O interfaces for manually controlling robotic crawler 110, such as joysticks and other tactile controls, for navigation, deploying sensors, and conducting various test protocols. Inspection module 178 may provide a plurality of routines for various inspection protocols using one or more sensor modules. In some embodiments, one or more sensor protocols are stored in sensor protocol data source 168 for use by inspection module 178. For example, a visual inspection protocol may include activating and capturing visual data from one or more sensor modules on robotic crawler 110 along a defined navigation path to enable mapping of captured visual data to location information with the machine. In some embodiments, a plurality of cameras with varying facings and/or positionable cameras may be present in one or more sensor modules 120, 122 and a visual inspection module may include selective activation and positioning of robotic crawler 110 and its various cameras. An inspection protocol executed by inspection module 178 may include a combination of navigational elements (navigation path, autonomous positioning, and/or manual positioning) and sensor protocols (position requirements, deployment, activation, timing/sampling, parameters, etc.). In some embodiments, inspection module 178 may define the storage of visual data and test data in visual data source 164 and test data source 166 and/or the display of visual data by visual display module 170 and test data by data display module 172. Crawler configuration module 180 may provide data regarding the configuration of modules and related capabilities and protocols for any given configuration of robotic crawler 110. In some embodiments, crawler configuration module 180 may map crawler configurations to machine specifications and sensor protocols to assist a user in matching inspection protocols with the resources available for a given test deployment. For example, a given configuration of sensor modules may define the test capabilities of robotic crawler 110 and recommend specific inspection protocols to utilize those sensor modules. In some embodiments, crawler configuration module 180 may include a library of sensor modules and related capabilities and support user reconfiguration of robotic crawler 110 for a desired inspection protocol. Crawler configuration module 182 may also define the set of crawler commands 184 that may be used to control robotic crawler 110. Crawler coordination module 182 may enable inspection control module 160 to control more than one robotic crawler 110 simultaneously. In some embodiments, crawler coordination module 182 may maintain a plurality of communication channels for control signals and data signals with a plurality of robotic crawlers. For example, crawler coordination module 182 may manage a plurality of instances of visual display module 170, data display module 172, autonomous navigation module 174, manual navigation module 176, inspection module 178, and crawler configuration module 180 for parallel management of the plurality of robotic crawlers. In some embodiments, crawler coordination module 182 may include interference protection for tracking the current crawler positions, navigation paths, and timing of various movements and sensor protocols to prevent collisions or other interference within the annular gap.

In some embodiments, visual display module 170, data display module 172, autonomous navigation module 174, manual navigation module 176, and inspection module 178 may include issuing one or more crawler commands 184 to robotic crawler 110 to complete some aspect of their function. Crawler commands 184 may then be translated into messages or control signals from control system 150 to robotic crawler 110. In some embodiments, crawler configuration module 180 may define the set of crawler commands available to the other modules based on the configuration of robotic crawler 110. An example set of crawler commands 184 are provided, but will be understood to be neither exclusive nor exhaustive of the possible crawler commands that could be used to control robotic crawler 110 and various configurations of traction modules, sensor modules, and body frame mechanics possible. Robotic crawler 110 may receive expand/contract commands 186 to expand or contract expandable body 112 between a collapsed state and one or more expanded states, such as a control signal to one or more motors that drive the body position. In some embodiments, expand or contract may be based on feedback from sensors within robotic crawler 110 when the traction modules are in a planar position (for collapsed state) or have contacted opposed surfaces in the annular gap (for expanded state). In other embodiments, expand or contract may be based on time (e.g., activate motor for x seconds of expansion or contraction) or distance (e.g., set crawler width to y inches). Robotic crawler 110 may receive move commands 188 to drive its traction modules forward or backwards (based on the present alignment of the traction modules in the case of multidirectional traction modules). Robotic crawler 110 may receive change direction commands 190 to reorient its traction modules and direction of travel. For example, change direction commands 190 may allow multidirectional traction modules to rotate 90 degrees and change from axial orientation and directions of travel to circumferential orientation and directions of travel. In some embodiments, change direction commands 190 may include orientation changes of greater or less than 90 degrees and include a feedback signal for confirming orientation or traction modules and communicating orientation back to control system 150. Robotic crawler 110 may receive traction mode commands 192 to drive changes in the configuration of the traction modules for different traction modes. For example, traction modules may include a flat mode for robot insertion and/or low profile and smooth surface travel and a clearance mode for providing clearance between the body of robotic crawler 110 and the surfaces it is moving along and/or traversing obstacles or uneven surfaces. Traction mode commands 192 may include control signals to change from flat mode to clearance mode or from clearance mode to flat mode. Robotic crawler 110 may receive position sensor commands 194 for sensor modules that include deployment and/or positioning features. For example, some sensor modules may include electromechanical features for extending, raising, lowering, rotating, or otherwise positioning one or more elements of the sensor module before, during, or after data collection. Position sensor commands 194 may include a control signal to activate a motor for extending or otherwise repositioning a sensor from robotic crawler 110 to position it for data collection or for moving a sensor (such as by rotation) independent of changing crawler position during data collection. Robotic crawler 110 may receive acquire data commands 196 for initiating data collection through a sensor module using whatever modality is present in that sensor module. Acquire data commands 196 may provide a start or stop signal for a continuous data collection mode, such as a video feed from the camera(s) of a visual sensor, or a specific test sequence for a more discrete sensor test, such as a mechanical wedge tightness test. It will be understood that some robotic crawlers and control systems may be able to communicate and manage multiple commands in parallel, as overlapping sequences, or as serial command series. Crawler coordination module 182 may enable control system 150 to issue commands to and acquire data from multiple robotic crawlers in parallel.

Figure 2:
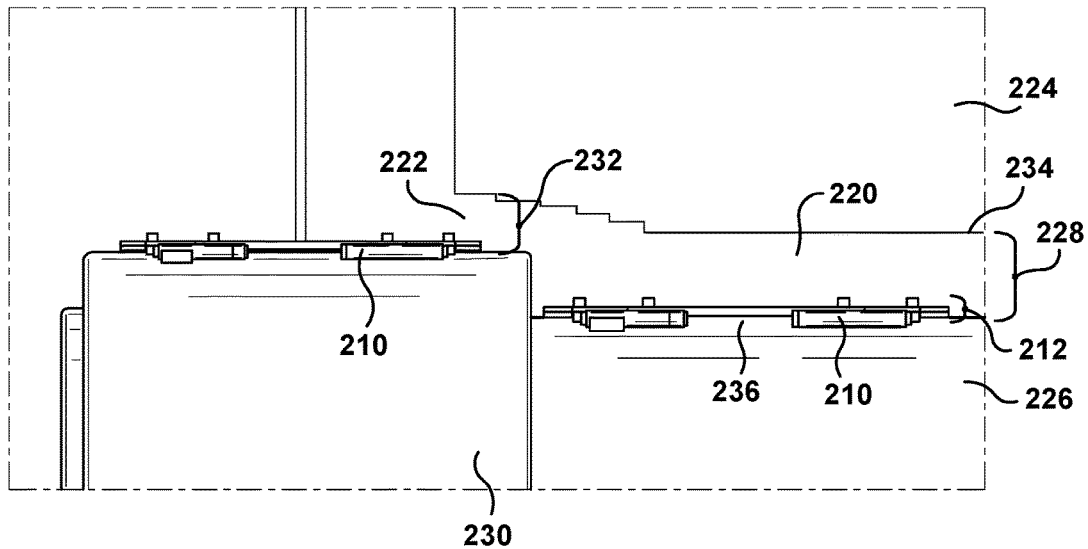
FIG. 2 shows a side section view of gap insertion of a robotic crawler into a machine.

Referring to FIG. 2, an in situ gap inspection system 200 is shown with a robotic crawler 210, such as robotic crawler 110 in FIG. 1, being inserted into a machine 202. Machine 202 may be any machine with an annular gap 220 accessible through an entrance gap 222 and, more specifically, a variety of machine configurations of generators, electric motors, or turbomachines. For example, a generator may allow insertion through the circumferential air gap between the core iron and the retaining ring permits in situ inspection of the rotor and the stator core. Annular gap 220 may be defined between a cylindrical central member 226 and a surrounding cylindrical member 224 with generally complementary curvature. In some embodiments, annular gap 220 may be an air gap generally defined by: the inner diameter of the stator minus the outer diameter of the rotor divided by two. Annular gap 220 has an axial length from a first end to a second end of cylindrical central member 226 and a circumference measured in the direction of the circumference of cylindrical central member 226. Annular gap 220 has an annular gap width 228 measured from outer surface 236 of cylindrical central member 226 to the nearest opposite surface (inner surface 234) of surrounding cylindrical member 224. In some embodiments, entrance gap 222 may be an air gap at an end of the central cylindrical member 226 and have the same entrance width as annular gap width 228. In other embodiments, entrance gap 222 may include additional features, such as a retaining member 230, that further constrain entrance gap 222 and define an entrance gap width 232 is that is less than annular gap width 228. In some embodiments, additional features or obstacles may reduce annular gap width 228, such entrance baffles used to direct cooling air flow.

In FIG. 2, robotic crawler 210 is in a collapsed state, where its traction modules are aligned in a single plane. Robotic crawler 210 is shown outside entrance gap 222 before insertion and inside annular gap 220 after insertion. Robotic crawler 210 may define a collapsed crawler width 212. Collapsed crawler width 212 may be less than both entrance gap width 232 and annular gap width 228. In its collapsed state, robotic crawler 210 engages only outer surface 236 of central cylindrical member 226 inside annular gap 220.

Figure 3:
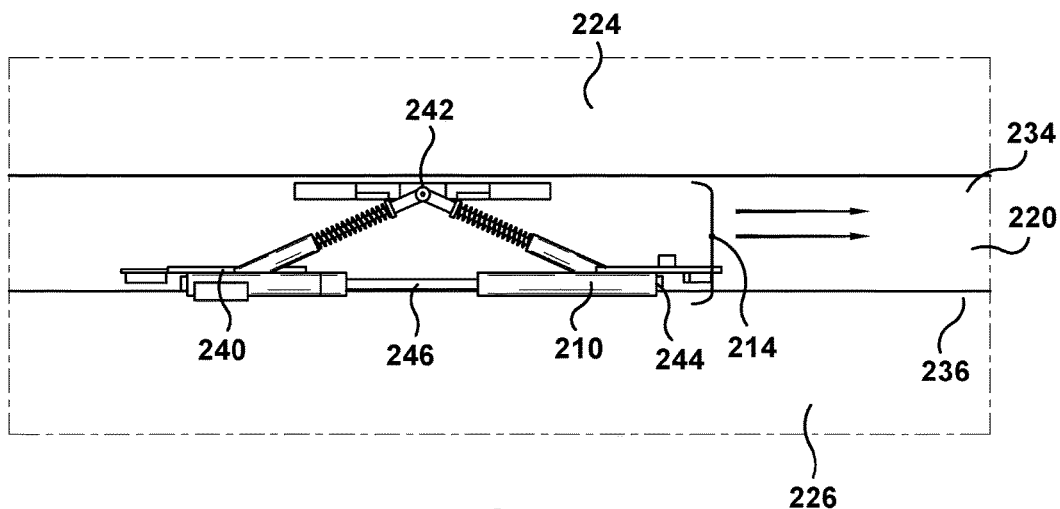
FIG. 3 shows a side section view of an expanded robotic crawler in the annular gap of a machine.
Figure 4:
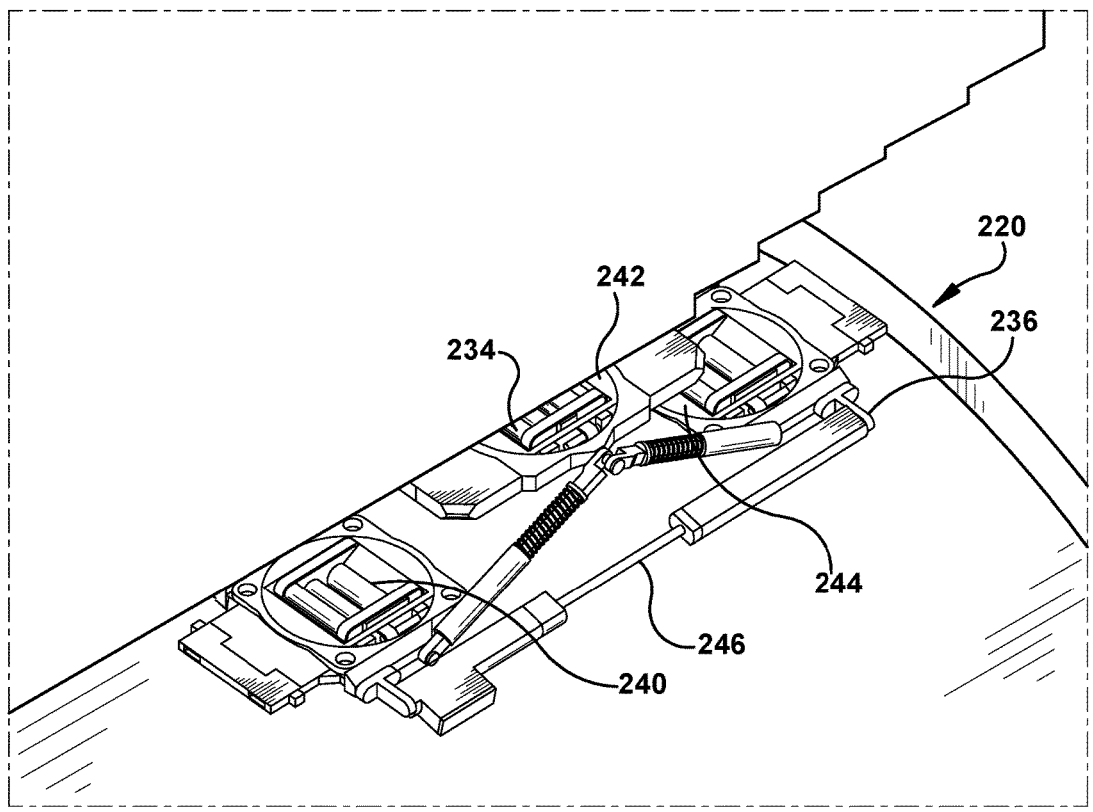
FIG. 4 shows a perspective cutaway view of an expanded robotic crawler in the annular gap of a machine.

FIGS. 3-4 show two views of robotic crawler 210 in an expanded state within annular gap 220. When robotic crawler 210 is in its expanded state, it may engage opposed surfaces 234, 236. In an expanded state, robotic crawler 210 may define an expanded crawler width 214. Expanded crawler width 214 may be larger than collapsed crawler width 212 and entrance gap width 232, and equal to annular gap width 228 such that surface contact may be maintained with opposed surfaces 234, 236. In some embodiments, robotic crawler 210 comprises a plurality of traction modules 240, 242, 244 mounted in an expandable body 246. Traction modules 240, 244 may engage only outer surface 236 of central cylindrical member 226 and traction module 242 may engage only inner surface 234 of surrounding cylindrical member 236. In some embodiments, the configuration of traction modules 240, 242, 244 may be reversed and traction modules 240, 244 may engage only inner surface 234 of surrounding cylindrical member 236 and traction module 242 may engage only outer surface 236 of central cylindrical member 226. Traction modules 240, 242, 244 may include rollers, including wheels, balls, or tracks, to move robotic crawler 210 through annular gap 220 based on moving surface contact with opposed surfaces 234, 236. Traction modules 240, 242, 244 may move robotic crawler 210 on a desired navigation path through annular gap 220.

Figure 5A:
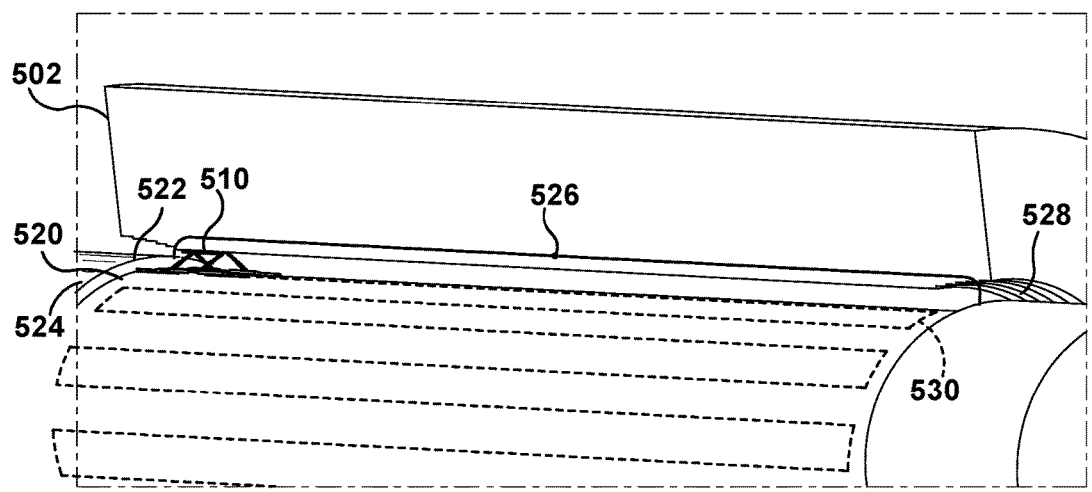
FIGS. 5A and 5B shows example inspection paths of a robotic crawler in the annular gap of a machine according to various embodiments of the disclosure.
Figure 5B:
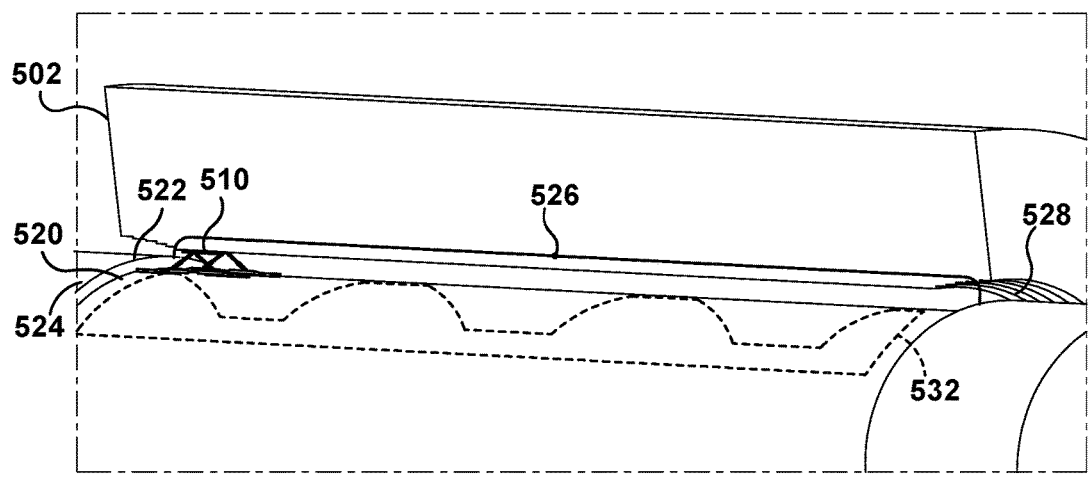

Referring to FIGS. 5A and 5B, another embodiment of a robotic crawler 510 is shown in an annular gap 520 with lines 530, 532 showing example navigation paths for inspecting annular gap 520. Robotic crawler 510 is shown in an expanded state in a starting crawler position just inside entrance gap 522 adjacent an entrance end portion 524 of the machine 502. Following line 530, robotic crawler 510 moves in a forward axial direction along a gap length 526 of annular gap 520 from the entrance end portion 524 to the closed end portion 528. In some embodiments, robotic crawler 510 may reach a step or other obstacle representing the end of the navigable gap length 526 of annular gap 520. For example, closed end portion 528 may include a step created by a retaining ring or other feature and may include another air gap into an enclosed end region of the machine. Robotic crawler 510 may include multidirectional traction modules that enable it to change its travel direction from the axial direction to the circumferential direction. Line 530 shows a number of circumferential steps along the circumference of annular gap 520. The length of the circumferential step may depend on a variety of factors related to sensor range/area (or field of view for visual sensors), test locations, desired test coverage or sampling, and/or specific machine features to be included in the navigation path to support desired test protocols using the sensor modules on robotic crawler 510. After a new circumferential position is achieved, line 530 shows a return path in the reverse axial direction along gap length 526. Robotic crawler 510 may reorient its movement direction back to an axial orientation and move in the opposite direction down the length of annular gap 520. In some embodiments, robotic crawler 510 may reach a step or other obstacle associated with entrance gap 522 and representing the end of the navigable gap length 526 of annular gap 520. Robotic crawler 510 may again reorient its travel direction for circumferential movement and make another circumferential step. Robotic crawler 510 may continue stepping through these axial passes at various circumferential positions along the circumference for the area of annular gap 520 to be inspected with the selected sensor modules and inspection protocol. In some embodiments, robotic crawler 510 may traverse gap length 236 in circumferential positions providing overlapping coverage for visual inspection around the entire circumference of annular gap 520 to provide a complete visual inspection of the surfaces of annular gap 520. Following line 532 shows an alternate inspection path and is provided to demonstrate that a plurality of inspection paths may be enabled by multidirectional and omnidirectional movement. Line 532 takes robotic crawler 510 along an inspection path that includes axial travel, circumferential travel, and travel along intermediate orientations between the axial and circumferential directions. More complex and less repetitious inspection paths may be used for inspection of specific areas or features, as well as to navigate around known obstacles.

Figure 6:
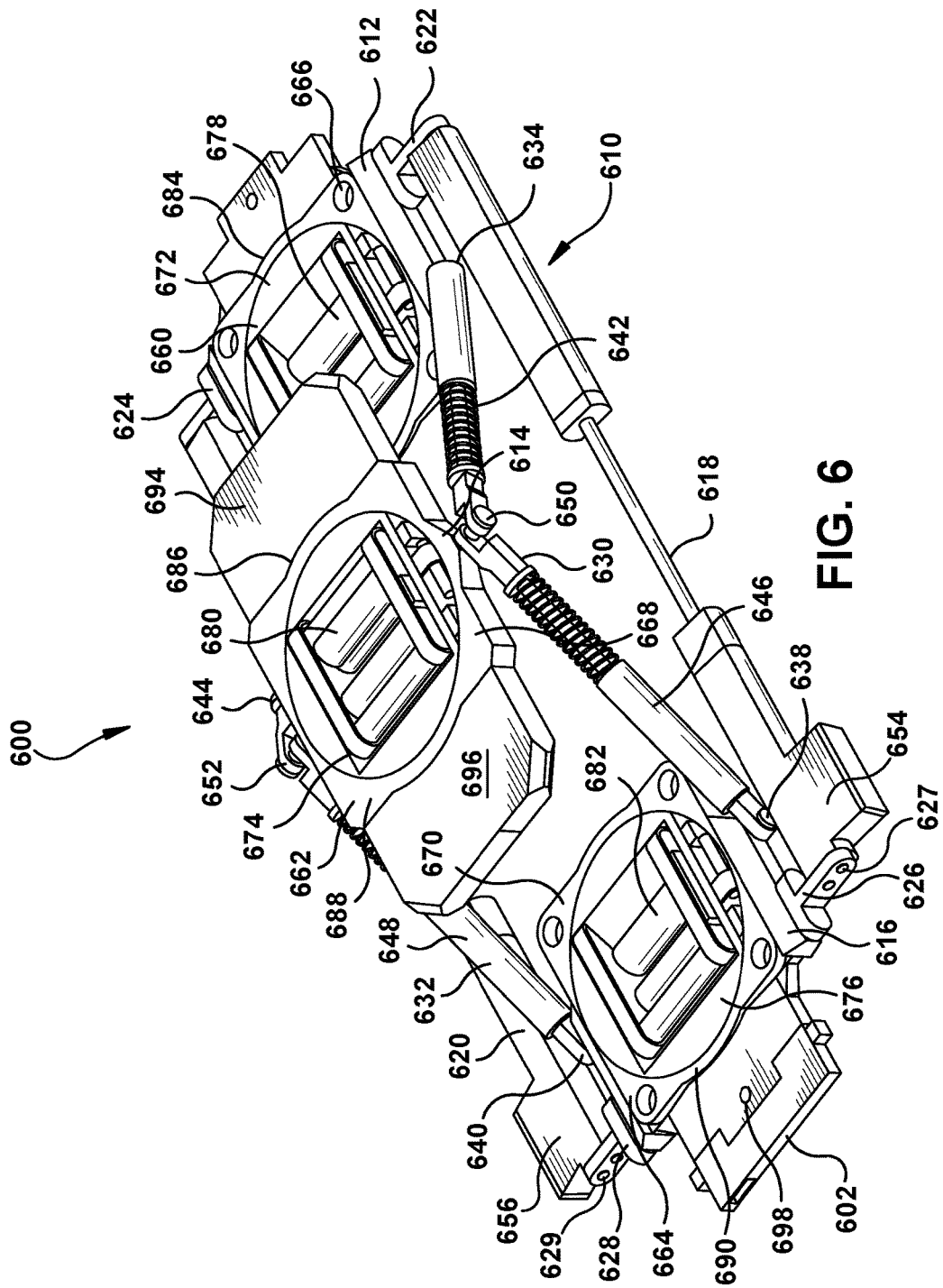
FIG. 6 shows a perspective view of a robotic crawler in its expanded state according to various embodiments of the disclosure.

Referring to FIGS. 6-8, an additional embodiment of a robotic crawler 600 is shown in several views and including an expanded state in FIG. 6 and a collapsed state in FIGS. 7-8. In some embodiments, robotic crawler 600 is a modular robot with an expandable body 610 including plurality of frames 612, 614, 616 for accommodating removable modules. Removable modules may include traction modules 660, 662, 664 that provide rollers, such as wheels, tracks, or balls, or another form of locomotion for moving robotic crawler 600 along the surfaces within a gap. Robotic crawler 600 may also accommodate a plurality of sensor modules, such as navigation sensors, visual inspection sensors, structural test sensors, or electrical test sensors, using sensor interfaces that provide mechanical and/or electrical/communication/control between robotic crawler 600 and the sensor modules. For example, one or more module frames may include sensor interfaces and/or the traction modules or other sensor modules may include sensor interfaces for chaining multiple modules from a single frame. The plurality of sensor interfaces may be provided at several positions on robotic crawler 600 to provide different operating positions for various sensors. For example, each of traction modules 660, 662, 664 may include one or more sensor interfaces and related sensor positions. In some embodiments, there may be multiple configurations of sensor interfaces. For example, sensor interfaces for attachment to traction modules 660, 662, 664 may be different than sensor interfaces between serial sensor interfaces. Other modules may also be provided for other functions, such as a tether connector module 602.

In some embodiments, expandable body 610 includes generally rectangular base frame and includes lateral members 618, 620 on the long sides of the rectangle, connected to front frame 612 and rear frame 616 providing the short sides of the rectangle. Lateral members 618, 620 may include frame attachments 622, 624, 626, 628 proximate their respective distal ends. Frame attachments 622, 624 may connect to front frame 612 and frame attachments 626, 628 may connect to rear frame 616. In some embodiments, middle frame 614 may be configured to be displaced from the plane of front frame 612 and rear frame 616 to expand the width of expandable body 610 in its expanded state. Middle frame 614 may be attached to extension link members 630, 632, which are connected to the rectangular base frame. For example, extension link members 630, 632 may include pivoting attachments 634, 636, 638, 640 with front frame 612 and rear frame 616 or, alternately, with lateral members 618, 620 proximate their distal ends. Extension link members 630, 632 may be articulated link members with first links 642, 644 and second links 646, 648 having pivoting attachments 650, 652 to middle frame 614. Pivoting attachments 650, 652 may act as an articulated joint in extension link members 630, 632 and move middle frame 614 perpendicular to the plane of the rectangular base frame. Expandable body 610 may include a motor or other actuator for moving middle frame 614. For example, lateral members 618, 620 may include linear actuators 654, 656 for moving front frame 612 relative to rear frame 616, changing the lengths of lateral members 618, 620 and the distance between front frame 612 and rear frame 616. When lateral members 618, 620 are in their fully extended positions, front frame 612, middle frame 614, and rear frame 616 may be in the same plane and expandable body 610 is in its narrowest or collapsed state. As lateral members 618, 620 are shortened by linear actuators 654, 656 and rear frame 616 moves toward front frame 612, extension link members 630, 632 articulate at pivoting attachments 650, 652 and first links 642, 644, second links 646, 648, and lateral members 618, 620 form an isosceles triangle with middle frame 614 moving in a direction perpendicular to the direction of movement between front frame 612 and rear frame 616. Other configurations of expandable bodies are possible, such as one or more frames being mounted on lever arms, scissor jacks, telescoping members, or other displacement mechanisms. In some embodiments, expandable body 610 may incorporate shock absorbers between front frame 612 and rear frame 616 and middle frame 614 to assist in navigating uneven gap spaces. For example, extension link members 630, 632 may incorporate telescoping links with an internal spring to assist with traction on opposed gap surfaces and compensate for some obstacles and/or changes in gap spacing. In some embodiments, lateral members 618, 620 may include emergency releases 627, 629 to disengage lateral members 618, 620 manually in the event of power loss or other failure that prevents control of linear actuators 654, 656. For example, frame attachments 626, 628 may incorporate mechanical fasteners that attach lateral members 618, 620 to frame attachments 626, 628 and these mechanical fasteners may act as emergency releases 627, 629 by enabling a user to release the mechanical fasteners and thereby disengage lateral members 618, 620 to cause expandable body 610 to collapse into its collapsed state. In some embodiments, emergency releases 627, 629 may be screws, bolts, or pins through frame attachments 626, 628 and into lateral members 618, 620 that may be removed to collapse expandable body 610. In some embodiments, expandable body 610 has a lateral shape that is an arc based on the configuration of frames 612, 614, 616 and lateral members 618, 620, most visible in FIG. 8. The arc of expandable body 610 may be configured to complement the curvature of an annular gap in which robotic crawler 600 is intended to operate. For example, the arc or curvature may be similar to the arc of the outer surface of the central cylindrical member or the inner surface of the surrounding cylindrical member that define the annular gap.

In some embodiments, each of frames 612, 614, 616 are configured to receive, position, and retain traction modules 660, 662, 664. For example, traction modules 660, 662, 664 may each be multidirectional traction modules with fixed outer frames 666, 668, 670 to removably attach to frames 612, 614, 616. Traction modules 660, 662, 664 may include rotating inner frames 672, 674, 676 that enable robotic crawler 600 to change the orientation of rollers 678, 680, 682 and direction of movement. Each of traction modules 660, 662, 664 may also include one or more interfaces 684, 686, 688, 690 that may be used to attach sensor modules or other functional modules, directly or in series. For example, traction module 660 may include interface 684 and is shown with a visual sensor module 692. Traction module 662 may include interfaces 686, 688 and visual sensor modules 694, 696. Traction module 664 may include interface 697, visual sensor module 698, and tether connector module 602.

Figure 9:
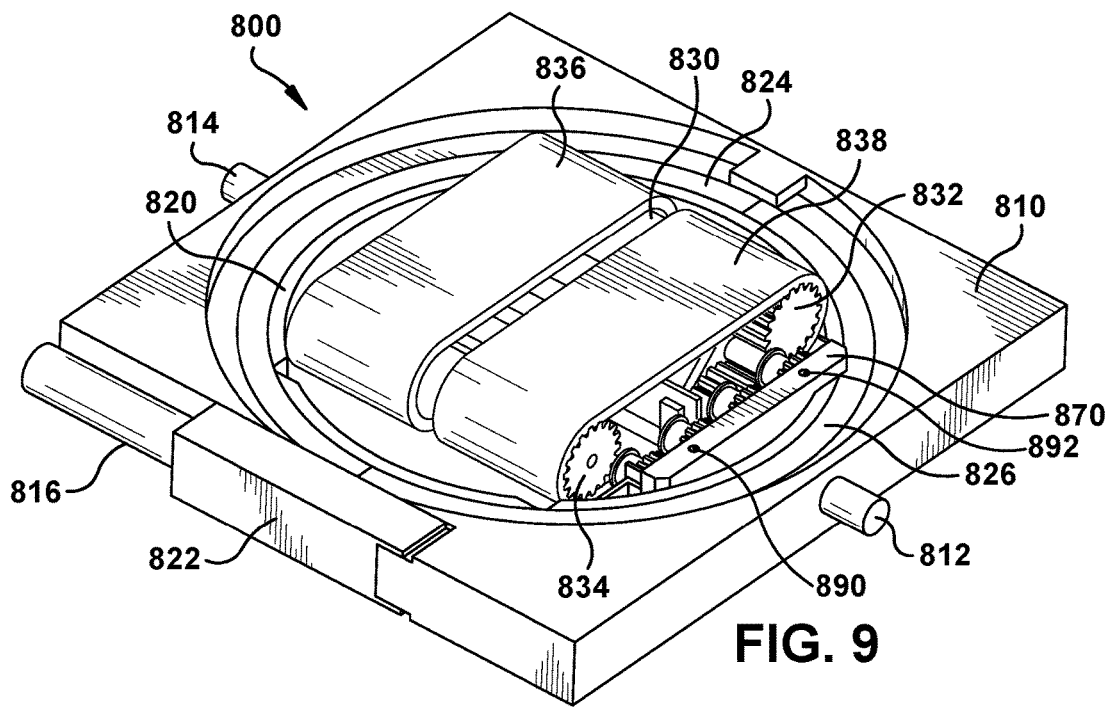
FIG. 9 shows a perspective view of a multidirectional traction module according to various embodiments of the disclosure.

FIG. 9 shows an example multidirectional traction module 800 according to various embodiments. Traction module 800 may be configured for use in a robotic crawler, such as robotic crawlers 110, 210, 510, 600. Traction module 800 enables the direction and orientation of travel of a robotic crawler to be changed without changing the orientation of the robotic crawler itself. Traction module 800 may include a fixed outer frame 810 with one or more attachment features 812, 814 configured for attachment to a robotic crawler, such as insertion into a body frame. In some embodiments, traction module 800 may also include an electrical interconnect 816 for power and/or control signals from the robotic crawler to traction module 800. Traction module 800 may include a rotating frame 820 seated within fixed outer frame 810 and capable of rotational movement relative to fixed outer frame 810. For example, rotating frame 820 or fixed outer frame 810 may include an actuator 822, such as a motor and worm gear for moving rotating frame 820. In some embodiments, rotating frame 820 may rotate 90 degrees to change the orientation and direction of travel. In some embodiments, rotating frame 820 may traverse or be stopped in various positions or orientations along at least a 90 degree arc and/or up to a 360 degree arc. In some embodiments, the worm gear or other drive mechanism incorporates an encoder to measure the angular position or orientation of rotating frame 820. For example, reference arcs 824, 826 may provide visual reference through reflective and non-reflective coatings to allow and optical sensor (not shown) to ascertain the orientation of traction module 800. Rotating frame 820 may provide a first position corresponding to forward and/or reverse (which may generally correspond to the axial direction within an annular gap). In some embodiments, roller assembly 830 is disposed within rotating frame 820 and includes a configuration of rollers 832, 834 for providing rotating traction to move the robotic crawler in a direction of rotation. Roller assembly 830 may also include a motor or other actuator for rotating rollers 832, 834. In some embodiments, roller assembly 830 may be driven in a forward or reverse direction in addition to changes in orientation from rotation of rotating frame 820. In some embodiments, rollers 832, 834 may engage and rotate belts 836, 838 to provide traction for traction module 800. For example, belts 836, 838 may substantially cover the length of rollers 832, 834 to provide a large contact area with adjacent machine surfaces. In some embodiments, belts 836, 838 may include surface features or treatments to improve traction, such as a textured surface for providing grip on oily surfaces. In some embodiments, roller assembly 830 may include a roller configuration actuator 870 to support multiple traction configurations and mechanisms for changing between configurations and locking the selected configuration in place. For example, roller assembly 830 may be capable of switching between a flat mode to provide a lower profile and an obstacle or clearance mode with angled belt paths for increasing the clearance between the robotic crawler and the surfaces it is traveling on. Roller configuration actuator 870 may actuate the change between the two modes and provide a locking mechanism for holding each configuration. In some embodiments, roller configuration actuator 870 may incorporate emergency releases 890, 892 that may be actuated to return roller assembly 830 to the flat mode in the event of a power failure or other loss of control of roller configuration actuator 870.

Figure 10:
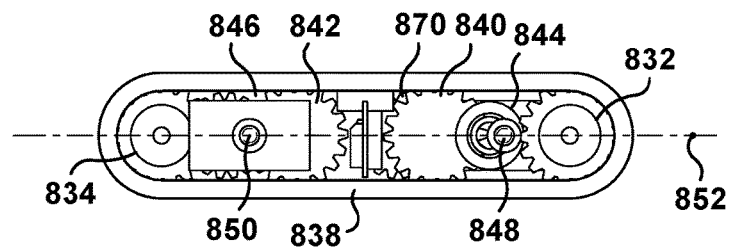
FIG. 10 shows a side section view of a traction assembly in its flat mode according to various embodiments of the disclosure.
Figure 11:
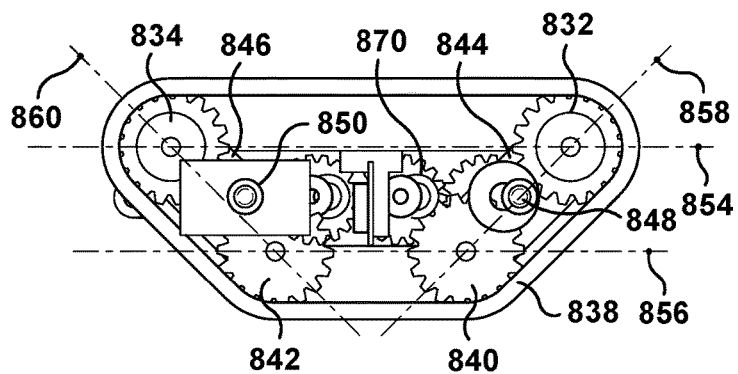
FIG. 11 shows a side section view of the traction assembly of FIG. 10 in its clearance mode.
Figure 12:
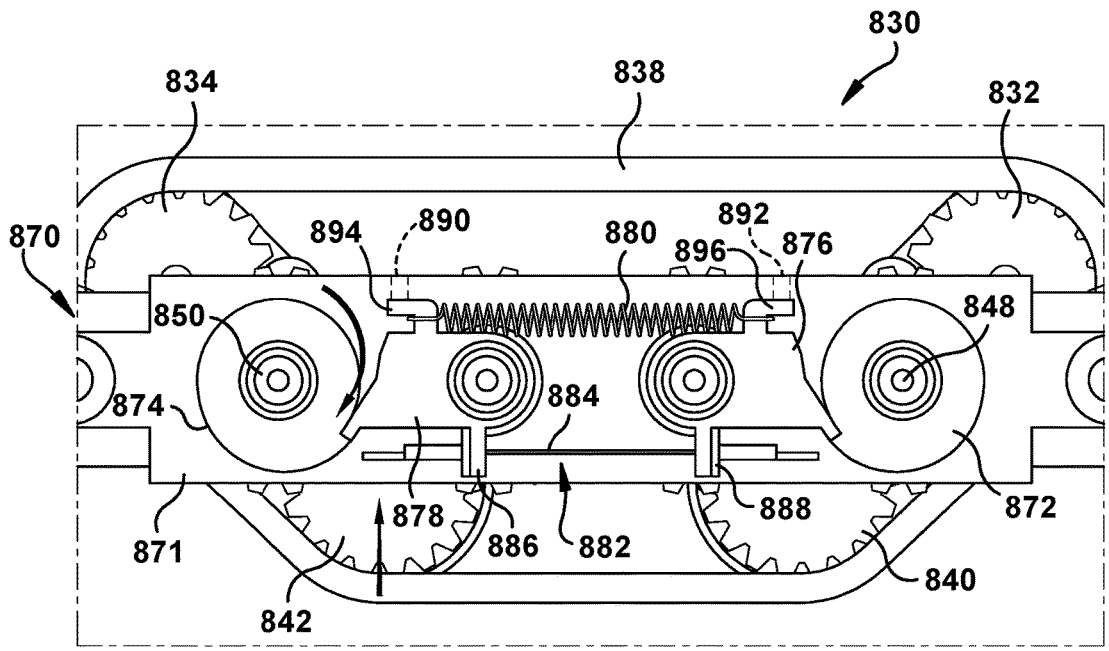
FIG. 12 shows a side section view of a position lock for the traction assembly of FIGS. 10-11.

FIGS. 10-12 show roller assembly 830 in flat mode (FIG. 10) and clearance mode (FIG. 11) and roller configuration actuator 870 (FIG. 12) for maintaining the two modes. Roller assembly 830 may have rollers 832, 834, 840, 842 in paired axle assemblies 844, 846. Axle assemblies 844, 846 may be rotatable around central pivot attachments 848, 850 to adjust between flat mode and clearance mode. In flat mode, each axis of rotation of rollers 832, 834, 840, 842 may be aligned in a single plane 852. In clearance mode, axle assemblies 844, 846 rotate rollers 832, 834, 840, 842 out of the shared plane and define at least two distinct planes 854, 856, 858, 860 of operation. For example, plane 854 aligns with the axis of rotation of rollers 832, 834 which support a parallel return path for belts 836, 838. Plane 856 aligns with axis of rotation of rollers 840, 842, which support a primary traction path for belts 836, 838. Plane 854 is distinct from plane 856. Plane 858 aligns with axis of rotation of rollers 832, 840 (on axle assembly 844) which supports a first climbing traction surface or return path (depending on the direction of travel). Plane 860 aligns with axis of rotation of rollers 834, 842 (on axle assembly 846) which supports a second climbing traction surface or return path (depending on the direction of travel). Once rollers 832, 834, 840, 842 are rotated out of common plane 852, a reaction force between the adjacent machine surface and primary traction surface may encourage reverse rotation to return to flat mode and a locking mechanism 871 may be included within roller configuration actuator 870 to counteract this tendency. In some embodiments, locking mechanism 871 may include ratchet ends 872, 874 on pivot attachments 848, 850 with claw members 876, 878 to engage ratchet ends 872, 874 and hold them in place in clearance mode under tensioning force from spring 880. A powered release mechanism 882 may be provided to controllably supply an opposing force to the tensioning force from spring 880. For example, a shape memory alloy wire 884 between two lever arms 886, 888 may contract when heated to release ratchet ends 872, 874 and allow roller assembly 830 to return to flat mode. An electric solenoid or other actuator may provide a similar powered release mechanism 882. Locking mechanism 871 may include manual emergency releases 890, 892. For example, emergency releases 890, 892 may be openings that provide access to manual release levers 894, 896 incorporated into locking mechanism 871 for holding roller assembly 830 in obstacle or clearance mode. In some embodiments, a pin or similar tool is guided manually into the openings of emergency releases 890, 892 to actuate manual release levers 894, 896. Other configurations for manually actuating emergency releases 890, 892 may include spring loaded buttons, spring pins, levers, or similar actuator members.

Figure 14:
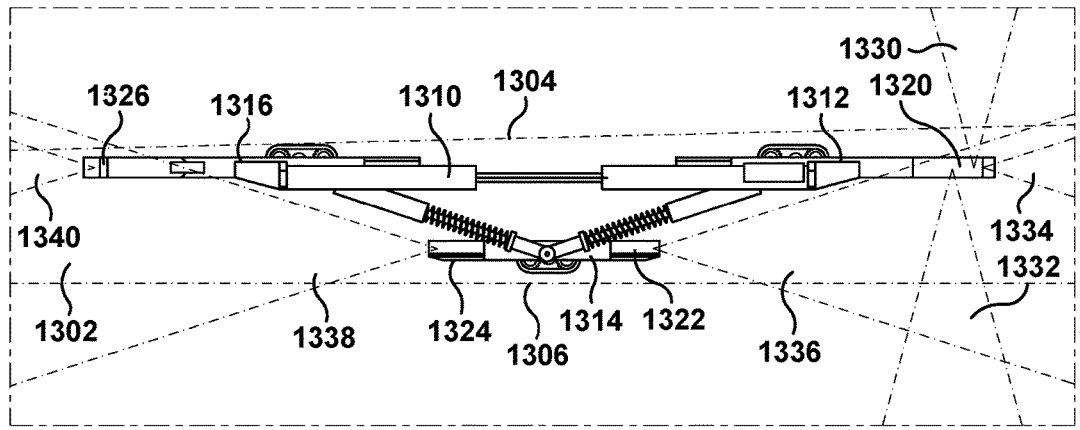
FIG. 14 shows a side view of a robotic crawler with example visual inspection and navigation fields of view.

Referring to FIG. 14, a cross-section view of an example connecting link 1200, such as may be used for first links 642, 644 or second links 646, 648, and incorporating a shock absorber is shown. Connecting link 1200 may include a first telescoping member portion 1210 and a second telescoping member portion 1212 held in movable relation to one another by a spring 1214. Note that other configurations of compactible but resistive link members are possible, including the use of pneumatic, fluid, or magnetic resistance between rigid members and/or the use of one or more flexible members. The force necessary to compact spring 1214 and shorten connecting link from its resting or maximum length to a compacted length may be configured by adjusting the spring constant and/or frictional forces resisting such displacement. In some embodiments, connecting link 1200 may include a displacement transducer 1220 or other sensor for detecting the change in length of connecting link 1200. Displacement transducer 1220 may generate a signal indicative of the length change and communicate that signal to the robotic crawler or a control system for the robotic crawler. In some embodiments, displacement transducer 1220 will be mated with a wireless communication subsystem for providing sensor data. In some embodiments, displacement transducer 1220 will have a wired connection to a data bus for sensor and other operational data within a robotic crawler. In some embodiments, displacement data from displacement transducer 1220 may be used to adjust the distance of the expanded state of the robotic crawler to compensate for changes in gap width or particular obstacles.

Figure 13:
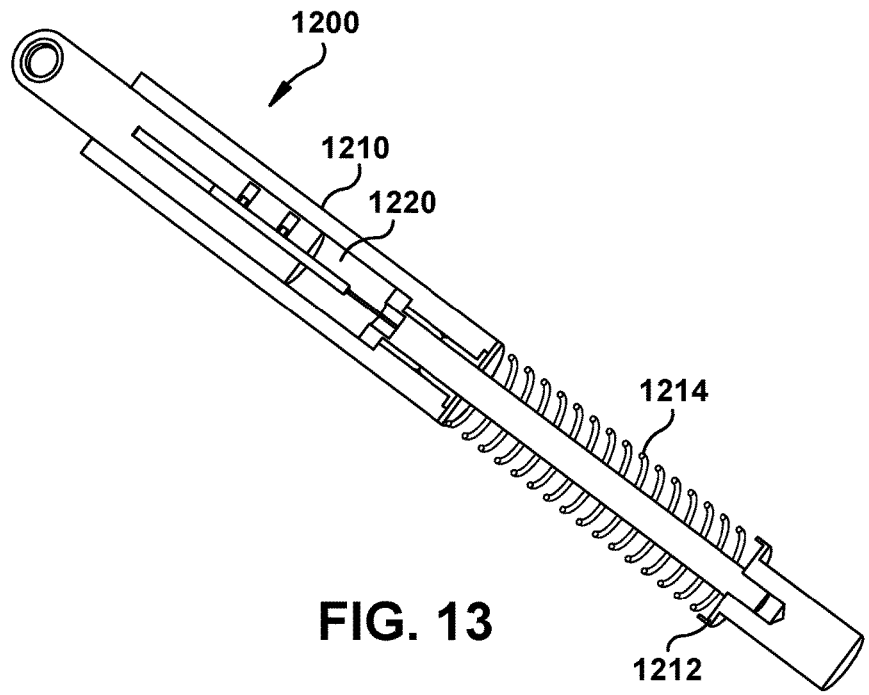
FIG. 13 shows a side cross-sectional view of an expansion link according to various embodiments of the disclosure.

Referring to FIGS. 14-17, an example configuration of visual sensor modules, including navigation modules, visual inspection modules, and combinations thereof, is shown on a robotic crawler 1310 in a gap 1302 between opposed machine surfaces 1304, 1306. Robotic crawler 1310 may include a front traction module 1312, a middle traction module 1314, and a rear traction module 1316 that provide positioning and a sensor interface for the visual sensor modules. In FIG. 13, a combination of four sensor modules 1320, 1322, 1324, 1326 is shown. Sensor module 1320 may be a visual inspection module including a plurality of cameras and connected to front traction module 1312. Sensor module 1320 may have a first surface field of view 1330, a second surface field of view 1332, and a gap field of view 1334. Sensor modules 1322, 1324 may be navigation sensor modules including single cameras oriented in the direction of travel, both being connected to middle traction module 1314. Sensor module 1322 may have a gap field of view 1336 in one (axial) direction and sensor module 1324 may have a gap field of view 1338 in an opposite (axial) direction. Sensor module 1326 may be an auxiliary sensor module with a single camera connected to rear traction module 1316. An auxiliary sensor module may accommodate another function, such as tether attachment or another type of test sensor, while still incorporating at least one camera for collecting visual data. Sensor module 1326 may have a gap field of view 1340 to the rear of the robotic crawler. In an alternate embodiment, sensor module 1326 is another visual inspection module including a plurality of cameras, but only one camera is active for auxiliary navigation while sensor module 1320 is being used for the primary inspection protocol.

Figure 15:
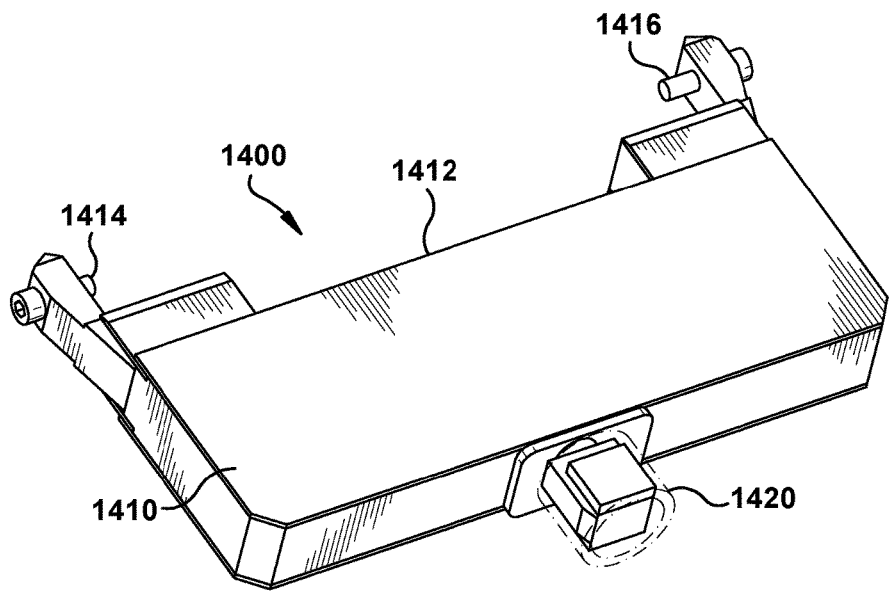
FIG. 15 shows top perspective view of an example navigation sensor module.

Referring to FIG. 15, an example navigation sensor module 1400 is shown. In some embodiments, navigation sensor module 1400 may include a module housing 1410 defining a mounting interface 1412 and accommodating fasteners 1414, 1416 for removably attaching navigation sensor module 1400 to a robotic crawler. For example, mounting interface 1412 may be configured for removable attachment to a sensor interface on a robotic crawler, such as a sensor interface on a module mounting frame or a previously installed module, including a traction module with a sensor interface. In some embodiments, module housing 1410 may include electronics, power source, communication channels, and/or optics for one or more visual sensors or cameras. In some embodiments, mounting interface 1412 may include a connector for power and/or communication channels for control and/or data signals to and from navigation sensor module 1400. Navigation sensor module 1400 may include a visual sensor for providing navigation data to a robotic crawler and/or control system. In some embodiments, navigation sensor module 1400 includes a camera 1420 mounted to or embedded in module housing 1410. For example, camera 1420 may be a forward mounted video camera with a single aperture to gather visual data in the direction it is aligned with (such as forward or backward in a gap space). In some embodiments, camera 1420 may incorporate a protective housing and/or include one or more components mounted inside module housing 1410. In some embodiments, camera 1420 may be mounted on a movable mounting that enables the field of view direction of camera 1420 to be adjusted relative to the position of navigation sensor module 1400 and the robotic crawler to which it is attached. For example, a movable mount may provide one or more pivoting adjustments that enable a user to change and set the direction of camera 1420 prior to insertion in a gap. Another movable mount may include powered adjustments that are configured for remote control through a sensor control bus in the robotic crawler or wireless communication with the robotic crawler and/or control system, enabling the field of view to be changed during operation of the robotic crawler within the gap of the machine. Camera 1420 may include other adjustable parameters, such as focus, aperture size, frame rates, and other settings for controlling visual data quality (or quantity). In some embodiments, navigation sensor module 1400 may include on or more light sources to improve visibility with camera 1420. In some embodiments, alternate navigation sensors may be used, including cameras with sensors for ultraviolet or infrared spectrums or other location technologies (e.g. sonar, RF beacons, magnetic imaging, etc.).

Figure 16:
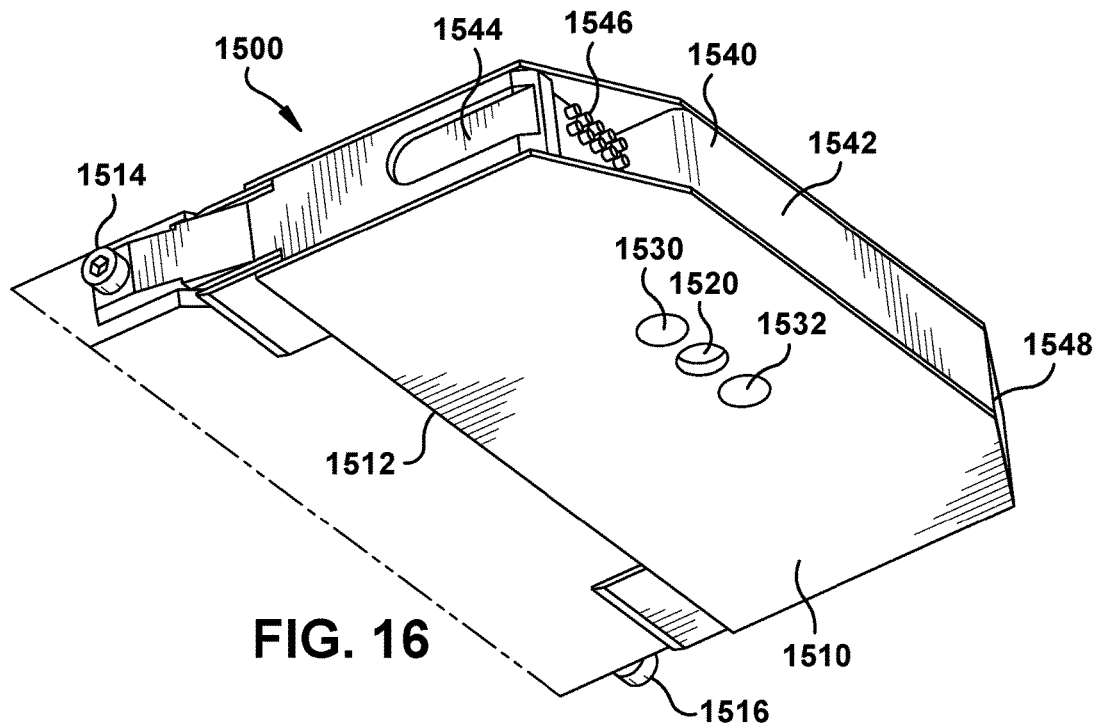
FIG. 16 shows a bottom perspective view of an example visual inspection sensor module.
Figure 17:
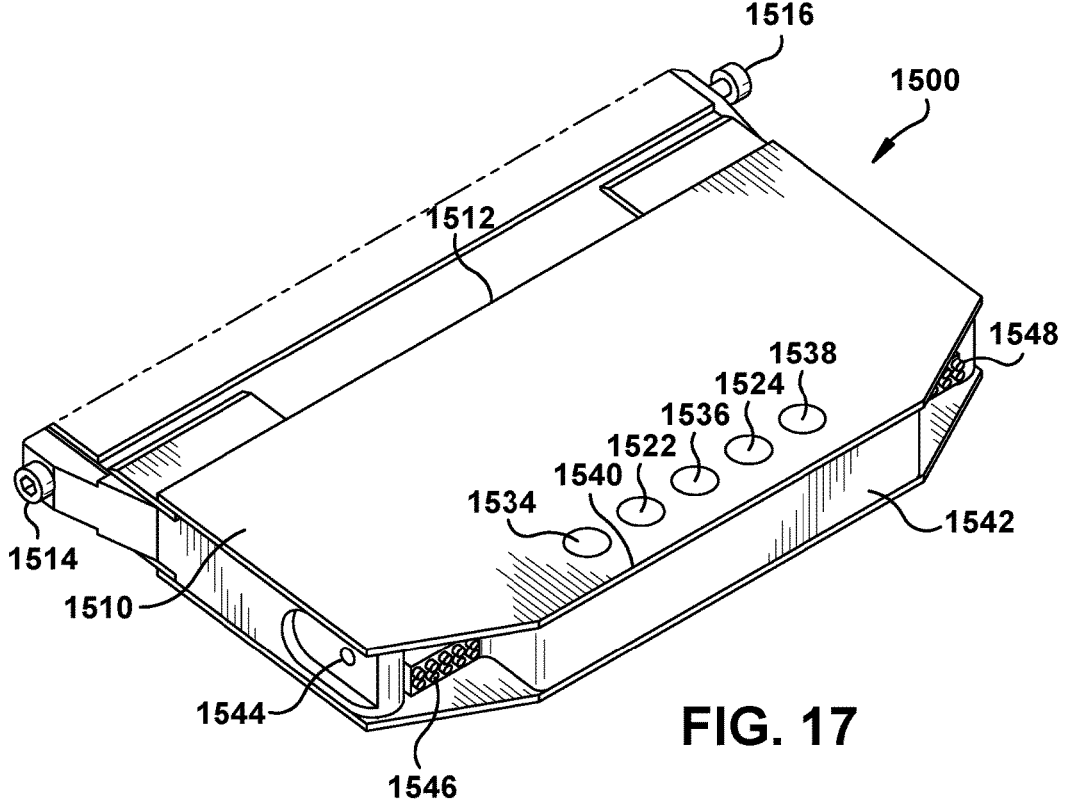
FIG. 17 shows a top perspective view of the example visual inspection sensor module of FIG. 16.

Referring to FIGS. 16-17, bottom and top views of an example visual inspection module 1500 are shown. In some embodiments, visual inspection module 1500 may include a module housing 1510 defining a mounting interface 1512 and accommodating fasteners 1514, 1516 for removably attaching visual inspection module 1500 to a robotic crawler. For example, mounting interface 1512 may be configured for removable attachment to a sensor interface on a robotic crawler, such as a sensor interface on a module mounting frame or a previously installed module, including a traction module with a sensor interface. In some embodiments, module housing 1510 may include electronics, power source, communication channels, and/or optics for one or more visual sensors or cameras. In some embodiments, mounting interface 1512 may include a connector for power and/or communication channels for control and/or data signals to and from visual inspection module 1500. Visual inspection module 1500 may include a plurality of visual sensors for providing visual data to a robotic crawler and/or control system. In some embodiments, visual inspection module 1500 includes cameras 1520, 1522, 1524 mounted to or embedded in module housing 1510. For example, camera 1520 may be a video camera oriented toward a first surface within a machine gap to gather visual data from the first surface as the robotic crawler moves along that surface. Cameras 1522, 1524 may be video cameras oriented toward a second surface opposite the first surface within the machine gap to gather visual data from the second surface as the robotic crawler moves along that surface. In some embodiments, cameras 1520, 1522, 1524 may be recessed inside module housing 1510 to prevent clearance issues with an adjacent machine surface. In some embodiments, cameras 1520, 1522, 1524 may include a variety of controls for position/direction of view, focus, field width, aperture size, frame rates, and other settings for controlling visual data quality (or quantity). Some or all of these adjustments may be manually set outside of the machine and/or are configured for remote control through a sensor control bus in the robotic crawler or wireless communication with the robotic crawler and/or control system, enabling dynamic adjustments during operation of the robotic crawler within the gap of the machine. In some embodiments, visual inspection module 1500 may include light sources 1530, 1532, 1534, 1536, 1538 to improve visibility with cameras 1520, 1522, 1524. For example, light sources 1530, 1532, 1534, 1536, 1538 may be LED lights with diffusers recessed into module housing 1510. In some embodiments, alternate inspection sensors may be used, including cameras with sensors for ultraviolet or infrared spectrums or other imaging technologies. In some embodiments, visual inspection module 1500 may include a sensor interface 1540 opposite mounting interface 1512. For example sensor interface 1540 may provide a mounting surface and/or power or signal interfaces for receiving the mounting interface of another sensor module to enable chaining of sensor modules. In some embodiments, sensor interface 1540 includes a mounting surface 1542, fastener receptacle 1544, and connectors 1546, 1548 for establishing a power, signal, and/or communication path between visual inspection module 1500 and a sensor module attached to sensor interface 1540.

Figure 18:
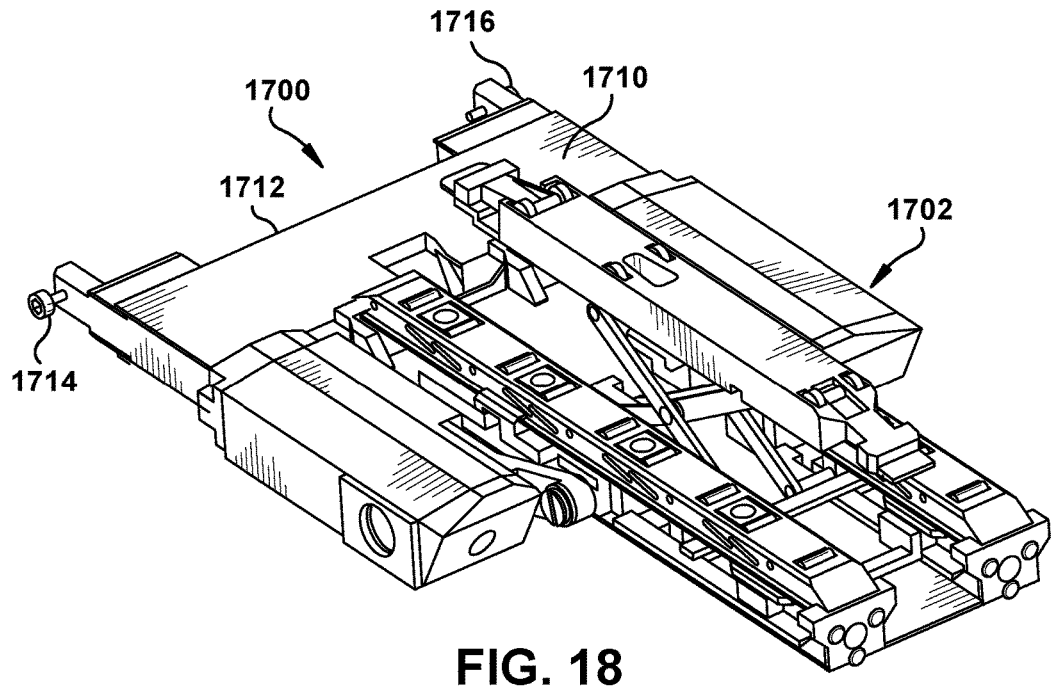
FIG. 18 shows a top perspective view of an example wedge tightness test sensor module.
Figure 19:
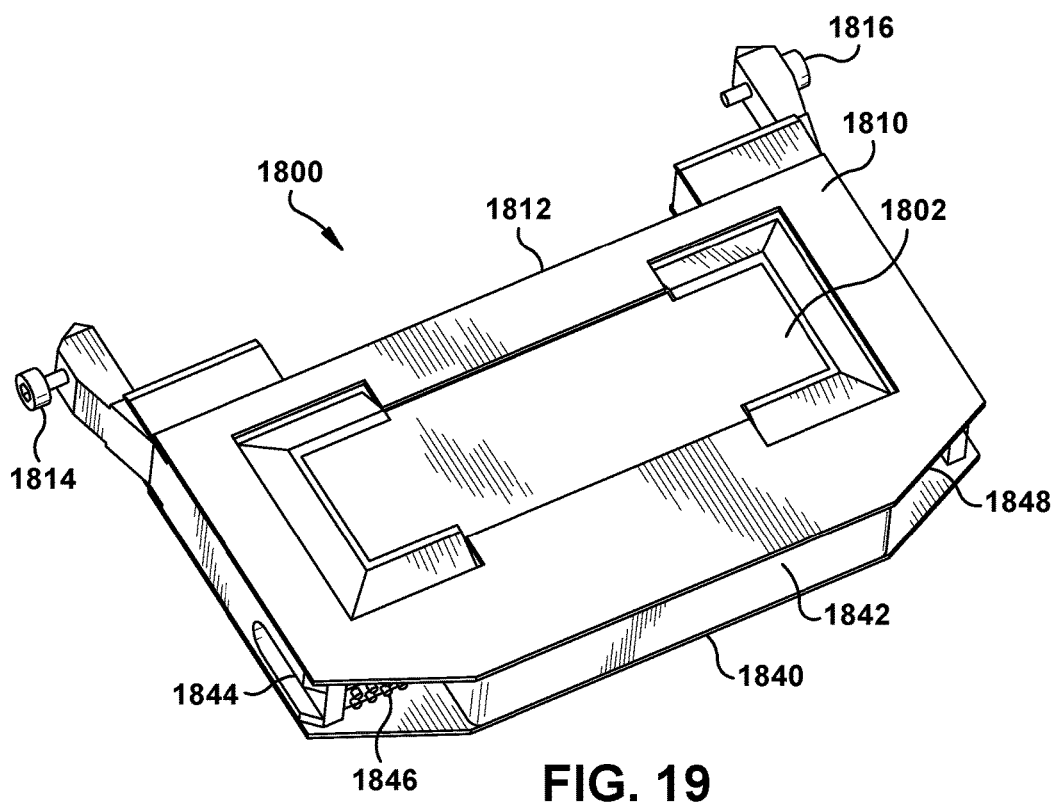
FIG. 19 shows a top perspective view of an example electromagnetic imperfection detection test sensor module.

Referring to FIGS. 18-19, example sensor modules are shown for removable attachment to sensor interfaces on a robotic crawler. These sensor modules are shown as examples of different types of sensor or test modules that may be created or adapted for use on a modular robotic crawler.

Wedge tightness assessment module 1700 may be an example of a mechanical test module. Wedge tightness assessment module 1700 may include a mechanical test assembly 1702 that may be deployed by the robotic crawler at a desired crawler positioning based on control signals from the robotic crawler or control system. Mechanical test assembly 1702 may provide test data back to the robotic crawler or control system. Mechanical test assembly 1702 may be connected to a module housing 1710 defining a mounting interface 1712 and accommodating fasteners 1714, 1716 for removably attaching wedge tightness assessment module 1700 to a robotic crawler. For example, mounting interface 1712 may be configured for removable attachment to a sensor interface on a robotic crawler, such as a sensor interface on a module mounting frame or a previously installed module, including a traction module with a sensor interface. In some embodiments, module housing 1710 may include electronics, power source, communication channels, and/or test components to support and/or interface with mechanical test assembly 1702. In some embodiments, mounting interface 1712 may include a connector for power and/or communication channels for control and/or data signals to and from wedge tightness assessment module 1700. In some embodiments, wedge tightness assessment module 1700 may include visual sensors, light sources, or other subsystems to assist in conducting the relevant test protocol. In the embodiments shown, wedge tightness assessment module 1700 may be a terminal sensor module because it does not include a sensor interface for receiving another sensor module.

Electromagnetic core imperfection detector module 1800 may be an example of an electrical test module. Electromagnetic core imperfection detector module 1800 may include an electrical test assembly 1802 that may be activated by the robotic crawler at a desired crawler positioning based on control signals from the robotic crawler or control system. Electrical test assembly 1802 may provide test data back to the robotic crawler or control system. Electrical test assembly 1802 may be connected to or embedded in a module housing 1810 defining a mounting interface 1812 and accommodating fasteners 1814, 1816 for removably attaching wedge tightness assessment module 1800 to a robotic crawler. For example, mounting interface 1812 may be configured for removable attachment to a sensor interface on a robotic crawler, such as a sensor interface on a module mounting frame or a previously installed module, including a traction module with a sensor interface. In some embodiments, module housing 1810 may include electronics, power source, communication channels, and/or test components to support and/or interface with electrical test assembly 1802. In some embodiments, mounting interface 1812 may include a connector for power and/or communication channels for control and/or data signals to and from electromagnetic core imperfection detector module 1800. In some embodiments, electromagnetic core imperfection detector module 1800 may include visual sensors, light sources, or other subsystems to assist in conducting the relevant test protocol. In some embodiments, electromagnetic core imperfection detector module 1800 may include a sensor interface 1840 opposite mounting interface 1812. For example sensor interface 1840 may provide a mounting surface and/or power or signal interfaces for receiving the mounting interface of another sensor module to enable chaining of sensor modules. In some embodiments, sensor interface 1840 includes a mounting surface 1842, fastener receptacle 1844, and connectors 1846, 1848 for establishing a power, signal, and/or communication path between visual inspection module 1800 and a sensor module attached to sensor interface 1840.

Figure 20:
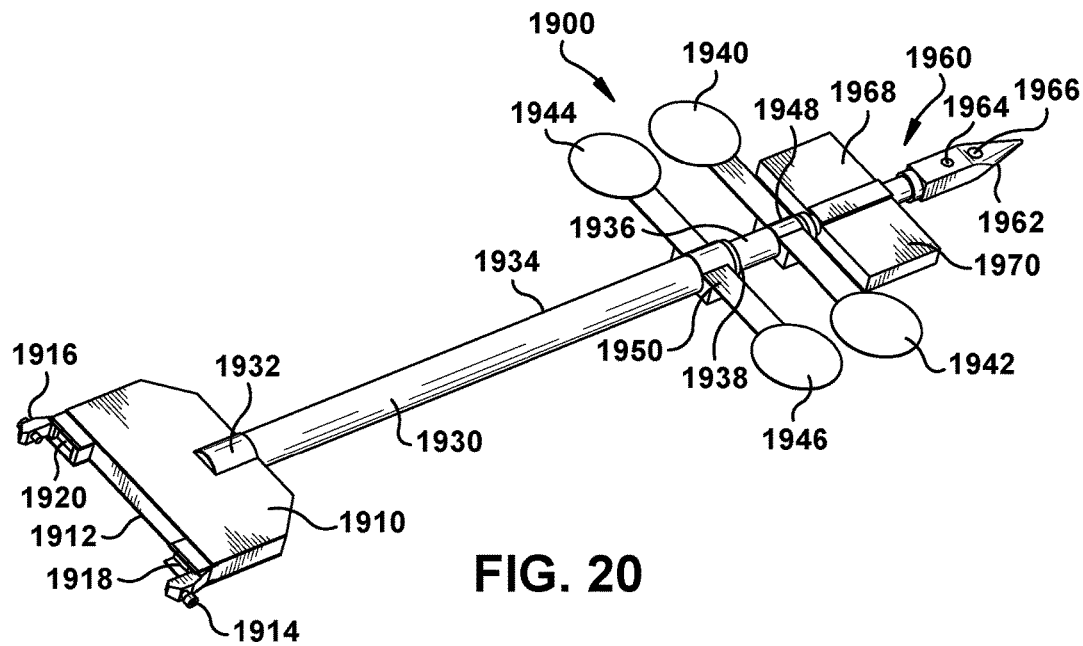
FIG. 20 shows a top perspective view of an example end region visual inspection sensor module.
Figure 21:
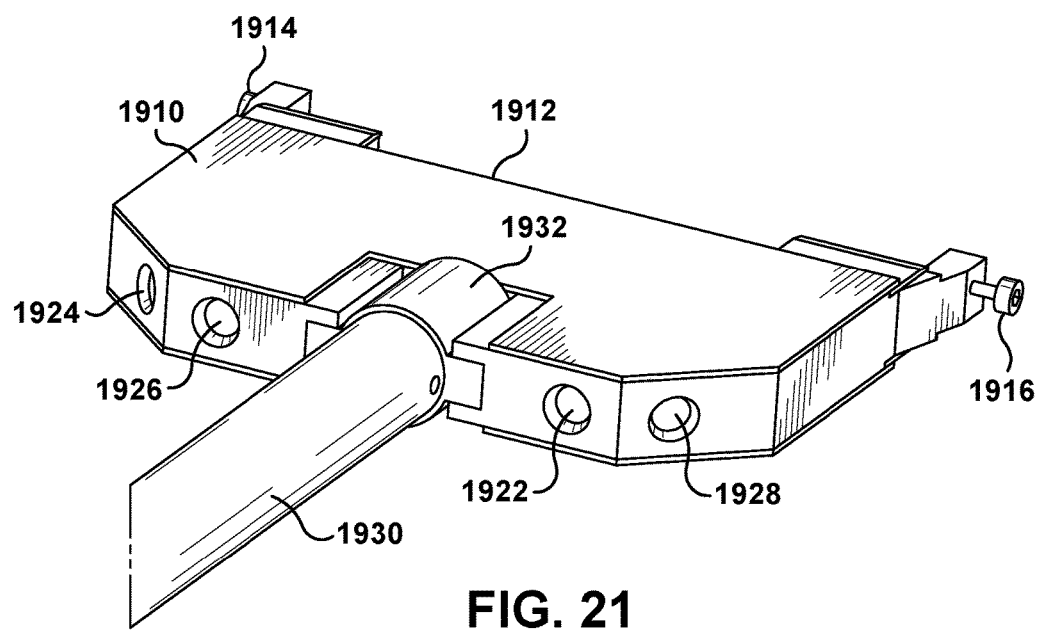
FIG. 21 shows a close-up top perspective of the connector assembly of the end region visual inspection sensor module of FIG. 20.

Referring to FIGS. 20-21, another configuration of a visual inspection sensor is shown as end region inspection module 1900, according to various embodiments. End region inspection module 1900 may be configured to extend into a region of a machine that a robotic crawler may not otherwise be able to reach and enable visual inspection of that region, such as an obstructed end region accessible through an inspection gap that is too narrow for the robotic crawler and/or inaccessible to the traction modules (or any other form of locomotion) of the robotic crawler. End region inspection module 1900 may include a module housing 1910 defining a mounting interface 1912 and accommodating fasteners 1914, 1916 for removably attaching end region inspection module 1900 to a robotic crawler. For example, mounting interface 1912 may be configured for removable attachment to a sensor interface on a robotic crawler, such as a sensor interface on a module mounting frame or a previously installed module, including a traction module with a sensor interface. In some embodiments, module housing 1910 may include electronics, power source, communication channels, and/or test components to support and/or interface with other test components of end region inspection module 1900. In some embodiments, mounting interface 1912 may include a connectors 1918, 1920 for power and/or communication channels for control and/or data signals to and from end region inspection module 1900. In some embodiments, end region inspection module 1900 may include a fixed camera 1922 and light sources 1924, 1926, 1928 mounted on or in module housing 1910. In some embodiments, end region inspection module 1900 includes an extension member 1930 connected to module housing 1910. For example, extension member 1930 may have a fixed mount 1932 to module housing 1910 and comprise a telescoping member with a fixed portion 1934, a telescoping portion 1936, and a slidably positionable joint 1938 between fixed portion 1934 and telescoping portion 1936. In some embodiments, the telescoping member may include an actuator in communication with the robotic crawler or the control system to adjust the length of the telescoping member during operation of the robotic crawler within the gap. In some embodiments, extension member 1930 further comprises one or more slidable supports that assist with positioning extension member 1930. For example, extension member 1930 may include slidable magnetic pads 1940, 1942, 1944, 1946 in laterally spaced pairs supported by brackets 1948, 1950. Slidable magnetic pads 1940, 1942, 1944, 1946 may combine a magnetic core configured to provide an attachment force to one or more magnetic surfaces of the machine with a non-stick pad surface configured to move along the magnetic surface. Slidable magnetic pads 1940, 1942, 1944, 1946 may be slidable on and detachable from the surface of the machine under the motive force of the robotic crawler, the telescoping member, or another positioning element. Slidable magnetic pads 1940, 1942, 1944, 1946 may be spaced laterally from extension member 1930 and their pad surfaces may define a plane for engaging with the surface of the machine. In one embodiment, one pair of slidable magnetic pads 1940, 1942 may be attached to telescoping portion 1936 and the other pair of slidable magnetic pads 1944, 1946 may be attached to fixed portion 1934. Note that while the example is shown with a configuration of four pads, other configurations with any number of pads may also be feasible. Extension member 1930 may connect to and support a rotatable camera assembly 1950 at the distal end of extension member 1930. In some embodiments, rotating camera assembly 1960 may include a rotating housing 1962 with a camera 1964, such as a digital video camera, and a light source 1966, such as an LED with diffuser. In some embodiments, rotating camera assembly 1960 may further include an electronics module 1968 and a motor module 1970. For example, electronics module 1968 may include electronics for processing visual data collected by camera 1964 and communicating that visual data to the robotic crawler or control system, such as by wired or wireless video streaming, and motor module 1970 may provide a motor, position index, and control interface for controllably moving rotating housing 1962, camera 1964, and light source 1966 during an inspection protocol.

Figure 22:
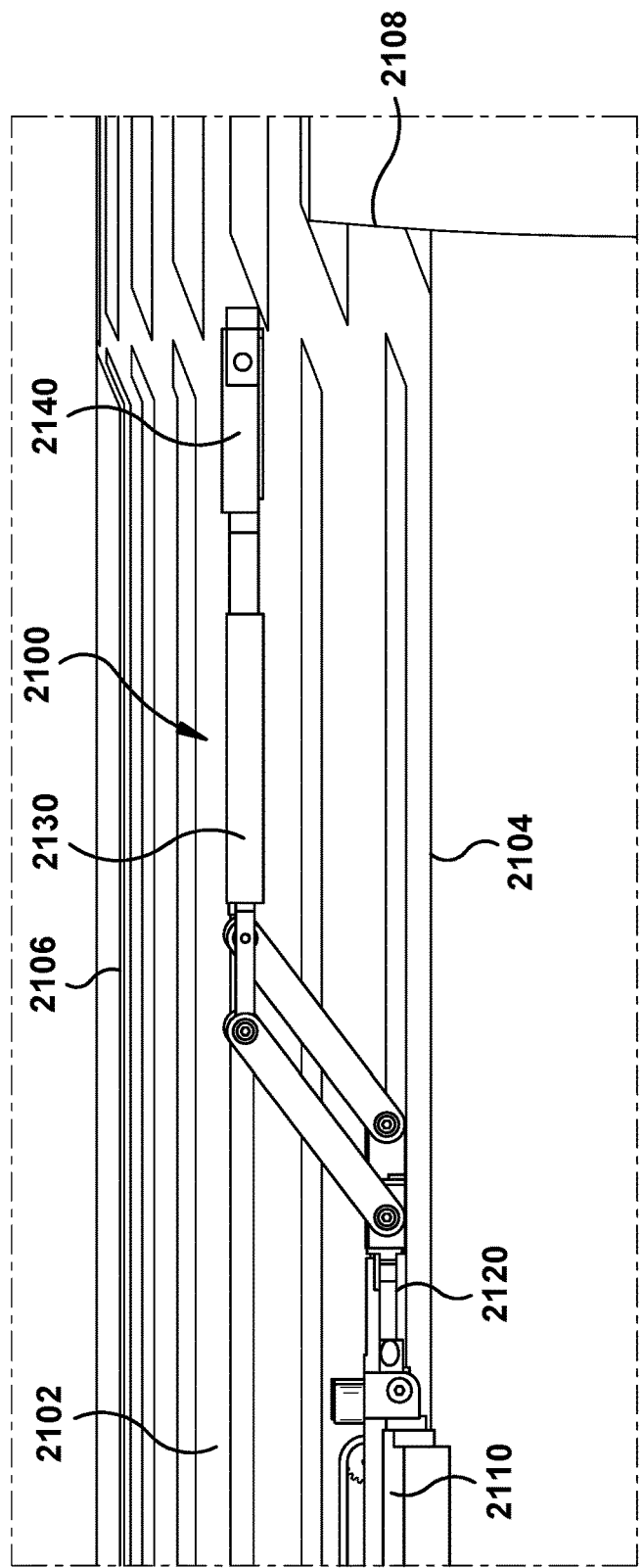
FIG. 22 shows a side cutaway view of an example deployment of an end region visual inspection sensor module in the annular gap of a machine.

Referring to FIG. 22, a mechanical positioning module 2100 is shown according to various embodiments. Mechanical positioning module 2100 may be used to position a sensor module within the gap and relative to a crawler position of a robotic crawler. For example, mechanical positioning module may include one or more positionable joints to move a sensor interface (and an attached sensor module) to a desired height between the machine surfaces that define the gap. Mechanical positioning module 2100 is shown in a gap 2102 between a first surface 2104 and a second surface 2106 and attached to a robotic crawler 2110 positioning a sensor interface housing 2140 to clear a lip 2108. In some embodiments, mechanical positioning module 2100 includes a mounting interface housing 2120 that connects to a sensor interface of robotic crawler 2110, a mechanical positioning assembly 2130 connected to mounting interface housing 2120 at one end, and sensor interface housing 2140 connected to the other end of mechanical positioning assembly 2130. For example, mounting interface housing 2120 may include a mounting interface similar to those described above for sensor modules and compatible with one or more sensor interfaces on robotic crawler 2110. Mounting interface housing 2120 may include a motor and other components for receiving control signals and controlling the position of mechanical positioning assembly 2130. Mechanical positioning assembly 2130 may include a variety of positionable joints, members, and actuators for performing the desired positioning operations, such as a parallel lift capable of raising and lowering sensor interface housing 2140 while maintaining it on plane parallel to the base of robotic crawler 2110. Sensor interface housing 2140 may provide a sensor interface similar to those described above for receiving, positioning, and connecting a sensor module. In some embodiments, sensor interface housing 2140 may be replaced with a sensor housing for an integrated sensor module with a positioning assembly.

Figure 23:
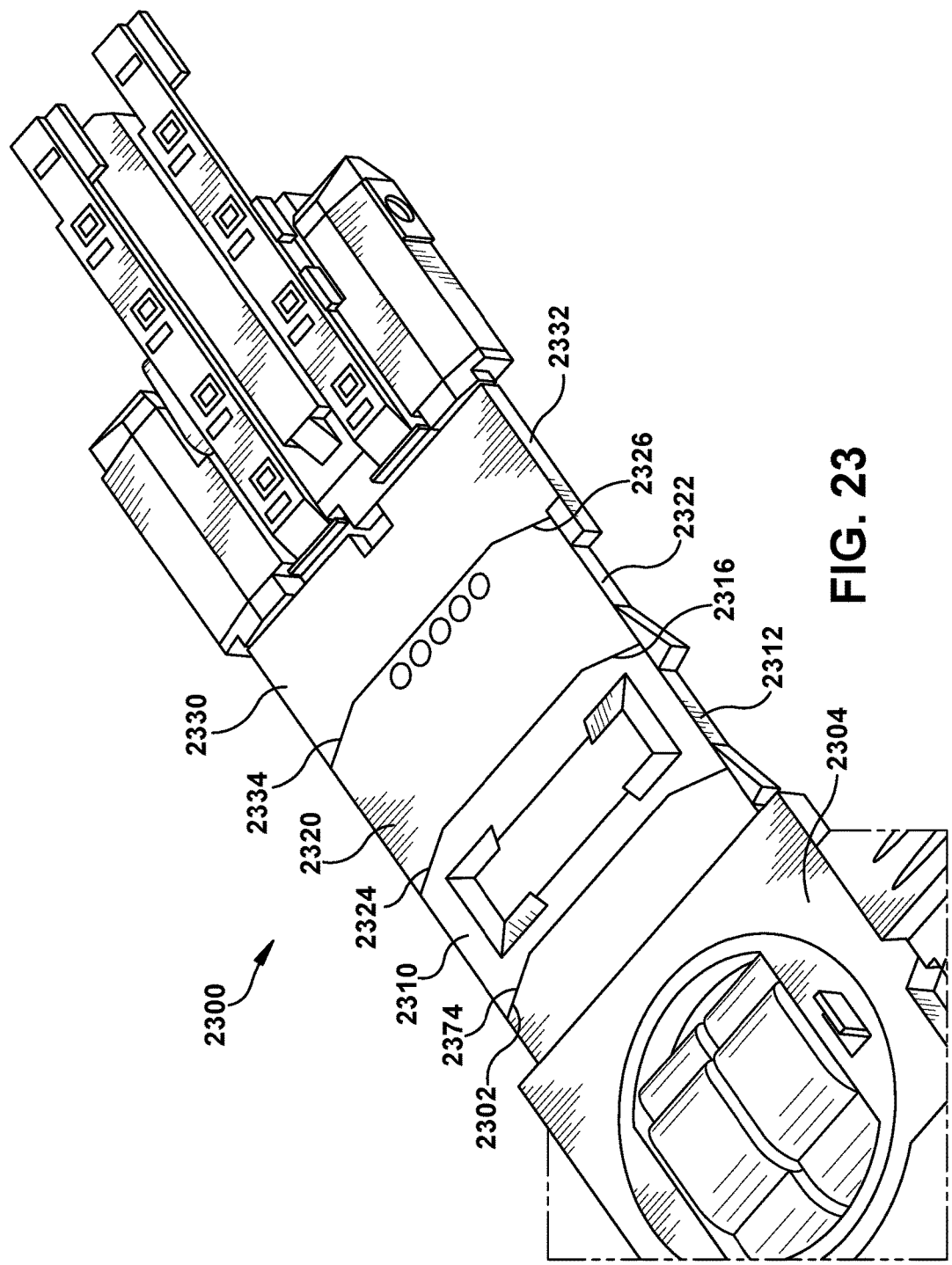
FIG. 23 shows a top perspective view of an example series of stacked modules.

Referring to FIG. 23, a stacked configuration 2300 of sensor modules 2310, 2320, 2330 is shown according to various embodiments. For example, sensor module 2310 may be an electrical test module similar to electromagnetic core imperfection detector module 1800 in FIG. 19. Sensor module 2320 may be a visual inspection module similar to visual inspection module 1500 in FIG. 17. Sensor module 2330 may be a mechanical test module similar to wedge tightness assessment module 1700 in FIG. 18. Sensor modules 2310, 2320, 2330 may be connected to a crawler sensor interface 2302 supported by a traction module 2304, providing electrical, mechanical, and communication connections to the robotic crawler. Sensor modules 2310, 2320, 2330 may each be activated and controlled by the robotic crawler independently at desired crawler positions based on control signals from the robotic crawler or control system. Any number of sensor modules 2310, 2320, 2330 may be stacked and controlled in this fashion to the limits of the mechanical strength of modules and interfaces, as well as robotic crawler balance and the limits of whatever power and communication paths the interface architecture supports. Sensor modules 2310, 2320, 2330 may each provide data back to the robotic crawler or control system independently. Each of sensor modules 2310, 2320, 2330 may be connected to or embedded in module housings 2312, 2322, 2332 defining mounting interfaces 2314, 2324, 2334 for removably attaching to the preceding sensor module or crawler sensor interface 2302. In some embodiments, mounting interfaces 2314, 2324, 2334 may provide robust mechanical interfaces to adjacent sensor interfaces, such that 2-5 sensor modules may be stacked. In some embodiments, module housings 2312, 2322, 2332 may include electronics, power sources or channels, communication channels, and/or test components to support and/or interface with their respective sensors. In some embodiments, mounting interfaces 2314, 2324, 2334 may include connectors for power and/or communication channels for control and/or data signals to and from sensor modules 2310, 2320, 2330. Sensor modules 2310, 2320 may include sensor interfaces 2316, 2326 opposite mounting interfaces 2314, 2324. For example, each mated pair of crawler sensor interface 2302 and sensor interfaces 2316, 2326 with mounting interfaces 2314, 2324, 2334 may include built in pins on one side and mating receptacles on the other side to establish operative electrical and/or signal contact between adjacent sensor modules 2310, 2320, 2330. Interconnected sensor modules 2310, 2320, 2330 may provide one or more continuous channels through their respective module housings 2312, 2322, 2332 to enable power and signals to pass through. In some embodiments, these continuous channels may include parallel channels enabling separate pathways to each of sensor modules 2310, 2320, 2330 and in some embodiments serial and/or multiplexed channels may be used. Sensor module 2330 may be a terminal sensor module that does not include a sensor interface and may only be used at the distal end of stacked configuration 2300. In stacked configuration 2300, sensor module 2310 may be connected to crawler sensor interface 2302 by mounting interface 2314 and to sensor module 2320 by sensor interface 2316. Sensor module 2320 may be connected to sensor module 2310 by mounting interface 2324 and to sensor module 2330 by sensor interface 2326. Sensor module 2330 may be connected to sensor module 2320 by mounting interface 2334 and may terminate the stack or chain of sensor modules 2310, 2320, 2330 extending from crawler sensor interface 2302. In some embodiments, sensor modules 2310, 2320, 2330 may be operated simultaneously to perform simultaneous inspections or tests independently or based on relationships between sensor modules 2310, 2320, 2330, the robotic crawler, and or other sensor modules mounted elsewhere on the robotic crawler.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A system comprising:
a robotic crawler having a plurality of multidirectional traction modules, an expandable body connected to the multidirectional traction modules, and a plurality of sensor modules, each of the plurality of sensor modules including a mounting interface, each mounting interface configured to attach to a sensor interface on the robotic crawler or one of the plurality of sensor modules, wherein the plurality of sensor modules are positioned relative to the plurality of multidirectional traction modules; and
a control system in communication with the robotic crawler, the control system providing a control signal to the robotic crawler to navigate an inspection path within an annular gap of a machine, wherein navigating the inspection path includes axial movement and circumferential movement of the plurality of multidirectional traction modules to inspect the machine using the plurality of sensor modules.

2. The system of claim 1, wherein the robotic crawler has a collapsed state and an expanded state, the collapsed state providing the robotic crawler with a first thickness less than an entrance gap width for the annular gap of the machine and the expanded state providing the robotic crawler with a second thickness greater than the entrance gap width and not greater than a working gap width for the annular gap of the machine, the machine selected from a generator, an electric motor, or a turbomachine.

3. The system of claim 2, wherein the robotic crawler includes at least one manual emergency release that transforms the robotic crawler from the expanded state to the collapsed state without a control signal from the control system.

4. The system of claim 1, wherein the plurality of multidirectional traction modules include a traction roller disposed within a rotatable frame, wherein the rotatable frame is controllably moved between a first position for axial movement and a second position for circumferential movement.

5. The system of claim 4, wherein the rotatable frame is controllably moved around a 360 degree arc for travel between the first position for axial movement and the second position for circumferential movement.

6. The system of claim 1, wherein the robotic crawler includes a communication channel in communication with the control system and a plurality of sensor interfaces disposed in physically separated portions of the robotic crawler, the plurality of sensor interfaces connected to the communication channel and each of the plurality of sensor interfaces providing a sensor data channel for at least one of the plurality of sensor modules.

7. The system of claim 1, wherein the plurality of sensor modules include a plurality of sensor types selected from navigation sensors, visual inspection sensors, structural test sensors, or electrical test sensors.

8. The system of claim 7, wherein the plurality of sensor modules include a first sensor module having a first sensor type and a second sensor module having a second sensor type different from the first sensor type.

9. The system of claim 1, wherein the control system provides fully automated inspection of all machine surfaces within the annular gap using the robotic crawler to follow a selected inspection path.

10. The system of claim 1, wherein the control system comprises a user interface displaying sensor data from the plurality of sensor modules and enables manual override of automated inspection navigation of the robotic crawler.

11. The system of claim 1, wherein the robotic crawler is one of a plurality of robotic crawlers operating within the annular gap of the machine and the control system is configured to communicate with the plurality of robotic crawlers and guide the plurality of robotic crawlers on a plurality of inspection paths.

12. The system of claim 1, further comprising a tether reel that manages a cable connected to the robotic crawler, wherein the tether reel includes a tension management function that automatically adjusts a cable tension during operation of the robotic crawler.

13. A method comprising:
inserting a robotic crawler into an annular gap of a machine;
expanding an expandable body of the robotic crawler such that a plurality of multidirectional traction modules on the robotic crawler engage opposed surfaces in the annular gap;
traversing an inspection path within the annular gap using axial movements and circumferential movements of the robotic crawler; and
performing a plurality of inspection tests along the inspection path using a plurality of sensor modules, each of the plurality of sensor modules including a mounting interface, each mounting interface attached to a sensor interface on the robotic crawler or one of the plurality of sensor modules, wherein the plurality of sensor modules is attached to the robotic crawler.

14. The method of claim 13, further comprising providing at least one control signal to the robotic crawler from a control system to control at least one of the expanding, traversing, and performing.

15. The method of claim 14, wherein the control system provides fully automated inspection of all machine surfaces within the annular gap using the robotic crawler to follow a selected inspection path, the machine selected from a generator, an electric motor, or a turbomachine.

16. The method of claim 14, further comprising displaying sensor data from the plurality of sensor modules through a user interface of the control system and manually overriding an automated navigation of the robotic crawler along the inspection path.

17. The method of claim 14, wherein the robotic crawler is one of a plurality of robotic crawlers operating within the annular gap of the machine and the at least one control signal includes a plurality of control signals to the plurality of robotic crawlers to simultaneously traverse a plurality of inspection paths within the annular gap.

18. The method of claim 13, further comprising:
collapsing the expandable body of the robotic crawler such that the plurality of multidirectional traction modules on the robotic crawler disengage at least one surface in the annular gap; and
removing the robotic crawler from the annular gap of the machine through an entrance gap, wherein the entrance gap has an entrance gap width that is less than an annular gap width of the annular gap.

19. The method of claim 18, wherein collapsing the expandable body of the robotic crawler includes actuating a manual emergency release without receiving a control signal from a control system to control the collapsing.

20. The method of claim 13, wherein traversing the inspection path includes controllably rotating traction rollers in the plurality of multidirectional traction modules between a first position for axial movement and a second position for circumferential movement.

21. The method of claim 20, wherein traversing the inspection path includes controllably rotating traction rollers in the plurality of multidirectional traction modules around a 360 degree arc for travel between the first position for axial movement and the second position for circumferential movement.

22. The method of claim 13, wherein the robotic crawler includes a plurality of sensor interfaces disposed in physically separated portions of the robotic crawler, the plurality of sensor interfaces connected to a communication channel and each of the plurality of sensor interfaces providing a sensor data channel for at least one of the plurality of sensor modules, the method further comprising removing a first sensor module from a selected sensor interface and connecting a second sensor module to the selected sensor interface.

23. The method of claim 13, wherein the plurality of sensor modules include a plurality of sensor types selected from navigation sensors, visual inspection sensors, structural test sensors, or electrical test sensors, wherein performing the plurality of inspection tests uses the plurality of sensor types.

24. The method of claim 13, further comprising automatically adjusting a cable tension of a cable connected to the robotic crawler during operation of the robotic crawler using a tether reel.

25. A robot control system comprising:
a crawler configuration module providing operating instructions for a robotic crawler having a plurality of multidirectional traction modules, an expandable body connected to the multidirectional traction modules, and a plurality of sensor modules, each of the plurality of sensor modules including a mounting interface, each mounting interface configured to attach to the expandable body or one of the plurality of sensor modules;
at least one inspection path definition correlating to an inspection path within an annular gap of a machine, the machine selected from a generator, an electric motor, or a turbomachine, and
an autonomous navigation module in communication with the robotic crawler to provide a control signal for the robotic crawler to traverse the inspection path using axial movements and circumferential movements of the plurality of multidirectional traction modules to inspect the machine using the plurality of sensor modules.

* * * * *